United States Patent [19]

Nestor et al.

[11] 4,318,905
[45] Mar. 9, 1982

[54] NONAPEPTIDE AND DECAPEPTIDE AGONISTS OF LUTEINIZING HORMONE RELEASING HORMONE CONTAINING HETEROCYCLIC AMINO ACID RESIDUES

[75] Inventors: John J. Nestor, San Jose; Gordon H. Jones; Brian H. Vickery, both of Cupertino, all of Calif.

[73] Assignee: Syntex (U.S.A.) Inc., Palo Alto, Calif.

[21] Appl. No.: 162,455

[22] Filed: Jun. 23, 1980

[51] Int. Cl.$^3$ ..................... A61K 37/00; C07C 103/52
[52] U.S. Cl. .......................... 424/177; 260/112.5 LH
[58] Field of Search .............. 260/112.5 LH; 424/177

[56] References Cited

U.S. PATENT DOCUMENTS

| | | | |
|---|---|---|---|
| 3,842,065 | 10/1974 | Rees | 260/112.5 LH |
| 3,972,859 | 8/1976 | Fujino et al. | 260/112.5 LH |
| 3,992,365 | 11/1976 | Beddell et al. | 260/112.5 LH |
| 4,075,191 | 2/1978 | Beddell et al. | 260/112.5 LH |
| 4,089,946 | 5/1978 | Foell et al. | 260/112.5 LH |

OTHER PUBLICATIONS

Rivier, et al., Peptides, 1976, pp. 427–451.
Yanaihara, et al., Biochem. and Biophys. Res. Commun., vol. 52, No. 1 (1973), 64–73.
Fujino, et al., Biochem. and Biophys. Res. Commun., vol. 60, No. 1 (1974), 406–412.
Fujino et al., Biochem. and Biophys. Res. Commun., vol. 57, No. 4 (1974), 1248–1256.

*Primary Examiner*—Delbert R. Phillips
*Attorney, Agent, or Firm*—Kate H. Murashige; Alan M. Krubiner; Tom M. Moran

[57] ABSTRACT

Nonapeptide and decapeptide analogs of LH-RH of the formula

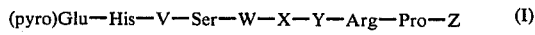

(pyro)Glu—His—V—Ser—W—X—Y—Arg—Pro—Z    (I)

and the pharmaceutically acceptable salts thereof wherein:

V is tryptophyl, phenylalanyl or 3-(1-naphthyl)-L-alanyl;
W is tyrosyl, phenylalanyl or 3-(1-pentafluorophenyl)-L-alanyl;
X is a D-amino acid residue of the formula:

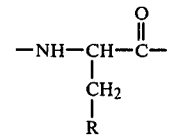

wherein R is a heterocyclic aryl containing radical selected from the group consisting of radicals represented by the following structural formulas:

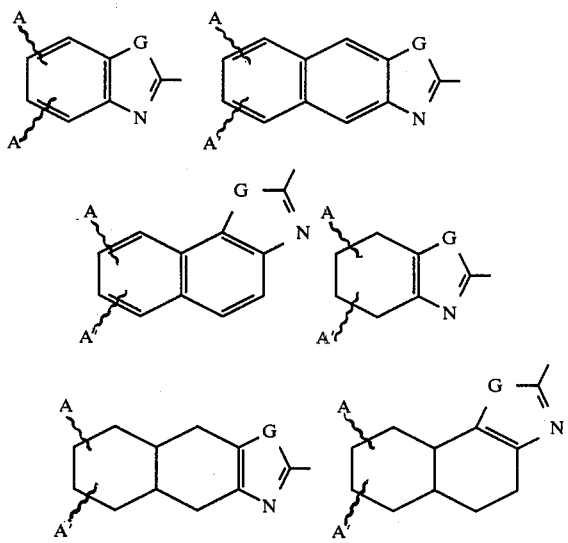

wherein A and A' are independently selected from the group consisting of hydrogen, lower alkyl, chlorine, and bromine, and G is selected from the group consisting of oxygen, nitrogen, and sulfur;
Y is leucyl, isoleucyl, nor-leucyl or N-methyl-leucyl;
Z is glycinamide or —NH—R$^1$, wherein:
R$^1$ is lower alkyl, cycloalkyl, fluoro lower alkyl or

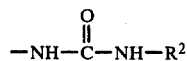

wherein
R$^2$ is hydrogen or lower alkyl,
are disclosed. These compounds exhibit potent LH-RH agonist properties.

22 Claims, No Drawings

NONAPEPTIDE AND DECAPEPTIDE AGONISTS OF LUTEINIZING HORMONE RELEASING HORMONE CONTAINING HETEROCYCLIC AMINO ACID RESIDUES

BACKGROUND OF THE INVENTION

Luteinizing hormone (LH) and follicle-stimulating hormone (FSH) are released from the anterior pituitary gland under the control of the releasing hormone LH-RH produced in the hypothalamic region. LH and FSH act on the gonads to stimulate the synthesis of steroid hormones and to stimulate gamete maturation. The pulsatile release of LH-RH, and thereby the release of LH and FSH, controls the reproductive cycle in domestic animals and humans. Additionally, LH-RH has effects in placenta, in releasing HCG, and directly on the gonads. Agonist analogs of LH-RH are useful for the control of fertility by two mechanisms of action. Low doses of LH-RH analogs can stimulate ovulation and are useful in the treatment of hypothalamic and ovulatory infertility. Additionally they can be used for hypogonadal conditions and impotence, and stimulate spermatogenesis and androgen production in the male. Paradoxically, larger doses of highly potent and long-lasting analogues of LH-RH have an opposite effect and block ovulation in the female and suppress spermatogenesis in the male. Related to these effects is a suppression of normal circulating levels of sexual steroids of gonadal origin, resulting in reduction in accessory organ weight in the male and the female. In domestic animals this paradoxical effect promotes weight gain in a feed-lot situation, stimulates abortion in pregnant animals and in general, acts as a chemical sterilant.

The natural hormone releasing hormone LH-RH is a decapeptide comprised of naturally occurring amino acids (which have the L-configuration except for the achiral amino acid glycine). Its sequence is as follows: (pyro) Glu-His-Trp-Ser-Tyr-Gly-Leu-Arg-Pro-Gly-NH$_2$. Many analogues of this natural material have been studied and the very large majority of them have proven to be of insufficient biological activity to be clinically useful. Certain select modifications have proven to have a beneficial effect on biological activity. By far the most significant modification is obtained by changing the 6-position residue from Gly to a D-amino acid. For example, replacing the Gly residue in the 6-position by D-Ala, D-Leu, D-Phe or D-Trp has led to a series of analogues of LH-RH with increased activity relative to LH-RH. See M. Monahan, et al, *Biochem.*, 12, 4616 (1973) for [D-Ala$^6$]LHRH; J. A. Vilchez-Martinez, et al, *Biochem. Biophys. Res. Comm.*, 59, 1226 (1974) for [D-Leu$^6$]LHRH and desGly$^{10}$[D-Leu$^6$, Pro-NHEt$^9$]LHRH; D. H. Coy, et al, *J. Med. Chem.*, 19, 423 (1976) for [D-Phe$^6$]LHRH; and W. Vale, et al, *Clinical Endocrinology*, 5th Supp., Blackwell Scientific Publications, Oxford, England (1976), p. 2615 and D. H. Coy, et al; *Biochem. Biophys. Res. Comm.*, 67, 576 (1979) for [D-Trp$^6$]LHRH.

In addition to the substantial increases in activity obtained by the above-referred to substitutions in position 6, further increases in activity may be obtained by removing the Gly-NH$_2$ in position 10 and then producing a nonapeptide as an alkyl-, cycloalkyl- or fluoroalkylamide derivative or by replacing Gly-NH$_2$ by an α-azaglycine amide. See for example, M. Fujino, et al, *Biochem. Biophys. Res. Comm.*, 49, 863 (1972), D. H. Coy, et al, *Biochem.* 14, 1848 (1975) and A. S. Dutta, et al, *J. Chem. Soc. Perkin I*, 1979, 379.

Substitution of N-methyl-leucine for the leucine residue in position 7 leads to increased stability towards enzymatic degradation. See for example, N. Ling, et al, *Biochem Biophys. Res. Comm.*, 63, 801 (1975).

Substitution of the tryptophan residue in position 3 by 3-(1-naphthyl)-L-alanine leads to an increase in biological potency. See for example, K. U. Prasad, et al, *J. Med. Chem.*, 19, 492 (1976) and Y. Yabe, *Chem. Pharm. Bull.*, 24 (12), 3149 (1976).

The tyrosine residue in position 5 can be replaced by phenylalanine or 3-(1-pentafluorophenyl)-L-alanine with the retention of substantial biological activity. See for example, N. Yanaihara, et al, *Biochem. Biophys. Res. Comm.*, 52, 64 (1973), and D. Coy, et al, *J. Med. Chem.*, 16, 877 (1973).

It would be desirable to prepare further analogues of LH-RH which have even a higher degree of biological activity than those heretofore described and which can be used clinically in animals and humans.

SUMMARY OF THE INVENTION

The present invention refers to novel nonapeptide and decapeptide derivatives of LH-RH which have, in the 6-position, certain lipophilic D-amino acids. The invention is also directed to various methods of use of these compounds and to pharmaceutical compositions therefor. A further aspect of the invention involves processes for the preparation of the novel compounds described above and to intermediates useful in such processes.

DETAILED DESCRIPTION OF THE INVENTION

The present invention relates to novel nonapeptide and decapeptide derivatives of LH-RH. More particularly the present invention relates to derivatives of LH-RH which have, in the 6-position, specific non-natural D-amino acid residues containing lipophilic heterocyclic residues, particularly residues containing a heterocyclic aryl ring fused to a carbocyclic ring system.

More specifically the compounds of the present invention are nonapeptides and decapeptides of the formula (pyro)Glu—His—V—Ser—W—X—Y—Arg—Pro—Z   (I)

and the pharmaceutically acceptable salts thereof wherein:

V is tryptophyl, phenylalanyl or 3-(1-naphthyl)-L-alanyl;

W is tyrosyl, phenylalanyl or 3-(1-pentafluorophenyl)-L-alanyl;

X is a D-amino acid residue of the formula:

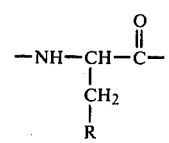

wherein R is a heterocyclic aryl radical selected from the group consisting of radicals represented by the following structural formulas:

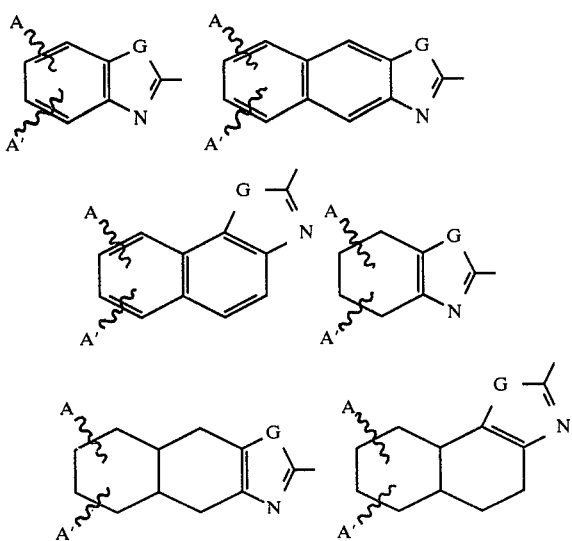

wherein A and A' are independently selected from the group consisting of hydrogen, lower alkyl, chlorine, and bromine, and G is selected from the group consisting of oxygen, nitrogen, and sulfur;

Y is leucyl, isoleucyl, nor-leucyl or N-methyl-leucyl;

Z is glycinamide or —NH—R$^1$, wherein

R$^1$ is lower alkyl, cycloalkyl, fluoro lower alkyl or

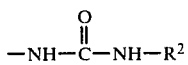

wherein:

R$^2$ is hydrogen or lower alkyl, are disclosed. These compounds exhibit potent LH-RH agonist properties.

As set forth above and for convenience in describing this invention, the conventional abbreviations for the various common amino acids are used as generally accepted in the peptide art as recommended by the IUPAC-IUB Commission on Biochemical Nomenclature, Biochemistry, 11, 1726 (1972) and represent L-amino acids with the exception of the achiral amino acid glycine and with the further exception of the amino acids in the 6-position designated by X. All peptide sequences mentioned herein are written according to the generally accepted convention whereby the N-terminal amino acid is on the left and the C-terminal amino acid is on the right.

As used herein, the term "pharmaceutically acceptable salts" refer to salts that retain the desired biological activity of the parent compound and do not impart any undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, naphthalenesulfonic acids, naphthalenedisulfonic acids, polygalacturonic acid; (b) salts with polyvalent metal cations such as zinc, calcium, bismuth, barium, magnesium, aluminum, copper, cobalt, nickel, cadmium, and the like; or with an organic cation formed from N, N'-dibenzylethylenediamine or ethylenediamine; or (c) combinations, of (a) and (b), e.g. a zinc tannate salt and the like.

As used herein the term "lower alkyl" refers to a straight or branched chain saturated hydrocarbon group having from 1 to 4 carbon atoms such as, for example, methyl, ethyl, n-propyl, isopropyl, n-butyl, isobutyl, sec-butyl and tert-butyl; the term "cycloalkyl group" refers to a cyclic saturated hydrocarbon group having from 3 to 6 carbon atoms, for example cyclopropyl, cyclobutyl, cyclopentyl and cyclohexyl; the term "fluoro lower alkyl" refers to a lower alkyl group wherein one or more hydrogen atoms are replaced by fluorine, such as, for example, trifluoromethyl, pentafluoroethyl, 2,2,2-trifluoroethyl, and the like.

As used herein "naphth" and "naphtho" are inclusive of 1,2-, 2,1- and 2,3-fused naphthalenes; "benzoxazole," "benzothiazole" and "benzimidazole" are inclusive of structures having substitutents at any or all of the positions of the phenyl ring; "naphthimidazole," "naphthoxazole" and "naphthothiazole" are inclusive of structures having substituents at any or all positions of the naphthalene ring; "tetrahydrobenzimidazole," "tetrahydrobenzoxazole" and "tetrahydrobenzothiazole" are inclusive of structures having substituents at any or all of the positions of the saturated ring; and "octahydronaphthimidazole," "octahydronaphthoxazole" and "octahydronaphthothiazole" are inclusive of cis- and trans-fused structures having substituents at any or all of the positions of the saturated rings.

Preferred compounds of this invention are those wherein X is 3-(2-benzimidazolyl)-D-alanyl or 3-[2-(4,5,6,7-tetrahydrobenzimidazolyl)]-D-alanyl; Z is glycinamide or prolylethylamide; V is tryptophyl or phenylalanyl; W is tyrosyl and Y is leucyl or N-methyl-leucyl. Particularly preferred compounds are (pyro) Glu-His-Trp-Ser-Tyr-3-(2-benzimidazolyl)-D-alanyl-Leu-Arg-Pro-Gly-NH$_2$, (pyro) Glu-His-Trp-Ser-Tyr-3-(2-benzimidazolyl)-D-alanyl-N-methyl-Leu-Arg-Pro-Gly-NH$_2$, (pyro) Glu-His-Phe-Ser-Tyr-3-(2-benzimidazolyl)-D-alanyl-Leu-Arg-Pro-Gly-NH$_2$, (pyro) Glu-His-Trp-Ser-Tyr-3-[2-(4,5,6,7-tetrahydrobenzimidazolyl)]-D-alanyl-Leu-Arg-Pro-Gly-NH$_2$, (pyro) Glu-His-Trp-Ser-Tyr-3-(2-benzimidazolyl)-D-alanyl-Leu-Arg-Pro-NHEt, and (pyro) Glu-His-Trp-Ser-Tyr-3-(2-benzimidazolyl)-D-alanyl-N-methyl-Leu-Arg-Pro-NHEt, and their pharmaceutically acceptable salts.

Especially preferred is (pyro)Glu-His-Trp-Ser-Tyr-3-(2-benzimidazolyl)-D-alanyl-Leu-Arg-Pro-Gly-NH$_2$ and its salts.

The compounds of this invention and, particularly, the salts thereof, exhibit surprisingly potent and long lasting LH-RH agonist activity in comparison to the previously most potent LH-RH agonists, namely (pyro)Glu-His-Trp-Ser-Tyr-D-Trp-Ser-Arg-Pro-Gly-NH$_2$ and the corresponding prolylethylamide. A primary measure of potency is the ability to partially or completely suppress estrus in normally cycling adult female rats (determined over a 2 week period) by twice daily subcutaneous injection.

Other bioassays which have been used for LH-RH analogues and which have been used for compounds of the present invention include:

(a) ovulation induction in diestrous or proestrous female rats by subcutaneous injection (Rippel, et al, *Proc. Soc. Exp. Biol. Med.,* 148, 1193 (1975)), (b) LH and FSH release by dispersed anterior pituitary cell cultures as measured by radioimmunoassay (Vale, et al, *Endocrinology,* 91, 562 (1972)), and (c) LH and FSH release into the peripheral circulation of ovariectomized, steroid treated rats in response to intravenous injection as measured by radioimmunoassay (Arimura, et al, *Endocrinology,* 90, 163 (1972)).

On a more advanced level, activity for these compounds may be demonstrated in vivo by depression of spermatogenesis and circulating and testicular levels of testosterone as well as dramatic reduction in prostate size in dogs suffering from benign prostatic hypertrophy.

As a result of the above the compounds may find use in a large variety of situations where control of LH and FSH, or direct gonadal action is important, including:

Physiological utilities (low dose effects)
ovulation induction in anovulatory infertility and for timed ovulation in female mammals;
therapy for infertility due to insufficient luteal function in women;
therapy for hypogonadotrophic or hypogonadal infertility in either sex-human.
therapy for cystic ovary/nymphomania syndrome in cattle;
induction or enhancement of sexual behavior or therapy for impotence/frigidity.
Paradoxical utilities (high dose effects)
female contraception;
ovulation suppression or delay;
induction of parturition;
synchronization of ovulation;
estrus suppression;
growth promotion in female animals;
luteolysis, menses induction;
early, first trimester abortifacient;
therapy for endometriosis;
therapy for mammary and cysts
therapy for polycystic ovary syndrome (Stein-Leventhal);
therapy for benign prostatic hypertrophy;
male contraception (inhibiting spermatogenesis);
therapy for diseases which result from excessive gonadal hormone production in either sex;
functional castration in male food producing animals;
suppression of proestrous discharge.

Another aspect of the present invention relates to particular uses for the above-described compounds, (including uses not heretofore described for LH-RH analogues) namely their uses for inhibiting ovulation (i.e. contraception) in the female, in the management of endometriosis, in the treatment of benign prostatic hypertrophy and in the inhibition of spermatogenesis (i.e. contraception) in the male. Thus, in these aspects, the invention is directed to a method useful for inhibition of ovulation, management of endometriosis, reduction of prostate size or inhibition of spermatogenesis in a mammalian subject having need of or desiring, said treatment which comprises administering to said subject an effective amount of a compound of the present invention as hereinabove described or a pharmaceutical composition containing same.

In the practice of the method of this invention an effective amount of a compound of the invention or a pharmaceutical composition containing same is administered to the subject in need of, or desiring, such treatment. These compounds or compositions may be administered by any of a variety of routes depending upon the specific end use, including orally, parenterally (including subcutaneous, intramuscular and intravenous administration), vaginally (particularly for contraception), rectally, buccally (including sublingually), or intranasally. The most suitable route in any given case will depend upon the use, particular active ingredient, the subject involved, and the judgment of the medical practitioner. The compound or composition may also be administered by means of slow-release, depot or implant formulations as described more fully hereinbelow.

In general for the uses hereinabove described, which are so-called "paradoxical" or high-dose uses, it is expedient to administer the active ingredient in amounts between about 0.001 and 100 µg/kg body weight per day, preferably between about 0.05 and 5.0 µg/kg body weight per day. This administration may be accomplished by a single daily administration, by distribution over several applications or by slow release in order to achieve the most effective results.

The exact dose and regimen for administration of these compounds and compositions will necessarily be dependent upon the needs of the individual subject being treated, the type of treatment, the degree of affliction or need and, of course, the judgment of the medical practitioner. In general, parenteral administration requires lower dosage than other methods of administration which are more dependent upon absorption. However, certain agents, such as dimethyl sulfoxide, appear to enhance the movement of LH-RH compounds through the skin.

A further aspect of the present invention relates to pharmaceutical compositions containing as active ingredient a compound of the present invention which compositions comprise such compound in admixture with a pharmaceutically acceptable non-toxic carrier. As mentioned above, such compositions may be prepared for use for parenteral (subcutaneous, intramuscular or intravenous) administration particularly in the form of liquid solutions or suspensions; for use in vaginal or rectal administration particularly in semisolid forms such as creams and suppositories; for oral or buccal administration particularly in the form of tablets or capsules; or intranasally particularly in the form of powders, nasal drops or aerosols.

The compositions may conveniently be administered in unit dosage form and may be prepared by any of the methods well-known in the pharmaceutical art, for example as described in Remington's Pharmaceutical Sciences, Mack Publishing Company, Easton, Pa., 1970. Formulations for parenteral administration may contain as common excipients sterile water or saline, polyalkylene glycols such as polyethylene glycol, oils of vegetable origin, hydrogenated naphthalenes and the like. Formulations for vaginal or rectal administration, e.g. suppositories, may contain as excipients, for example, polyalkyleneglycols, vaseline, cocoa butter, and the like. Formulations for inhalation administration may be solid and contain as excipients, for example, lactose or may be aqueous or oily solutions for administration in the form of nasal drops. For buccal administration typical excipients include sugars, calcium stearate, magnesium stearate, pregelatinated starch, and the like.

It is particularly desirable to deliver the compounds of the present invention to the subject over prolonged periods of time, for example, for periods of one week to one year from a single administration. Various slow release, depot or implant dosage forms may be utilized. For example, a dosage form may contain a pharmaceutically acceptable non-toxic salt of the compounds which has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzylethylenediamine or ethylenediamine; or (c) combinations of (a) and (b) e.g. a zinc tannate salt. Additionally, the compounds of the present invention or, preferably, a relatively insoluble salt such as those just described, may be formulated in a gel, for example, an aluminum monostearate gel with, e.g. sesame oil, suitable for injection. Particularly preferred salts are zinc salts, zinc tannate salts, pamoate salts, and the like. Another type of slow release depot formulation for injection would contain the compound or salt dispersed for encapsulated in a slow degrading, non-toxic, non-antigenic polymer such as a polylactic acid/polyglycolic acid polymer for example as described in U.S. Pat. No. 3,773,919. The compounds or, preferably, relatively insoluble salts such as those described above may also be formulated in cholesterol matrix silastic pellets, particularly for use in animals. Additional slow release, depot or implant formulations, e.g. liposomes, are well known in the literature. See, for example, "Sustained and Controlled Release Drug Delivery Systems", J. R. Robinson ed., Marcel Dekker, Inc., New York, 1978. Particular reference with respect to LH-RH type compounds may be found, for example, in U.S. Pat. No. 4,010,125.

The polypeptides of the present invention may be synthesized by any techniques that are known to those skilled in the peptide art. An excellent summary of the many techniques so available may be found in J. M. Stewart and J. D. Young, "Solid Phase Peptide Synthesis", W. H. Freeman Co., San Francisco, 1969, and J. Meienhofer, "Hormonal Proteins and Peptides", Vol. 2, p. 46., Academic Press (New York), 1973 for solid phase peptide synthesis and E. Schroder and K. Lubke, "The Peptides", Vol. 1, Academic Press (New York), 1965 for classical solution synthesis.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

A particularly preferred method of preparing compounds of the present invention involves solid phase peptide synthesis.

In this particularly preferred method the $\alpha$-amino function of the amino acids is protected by an acid or base sensitive group. Such protecting groups should have the properties of being stable to the conditions of peptide linkage formation, while being readily removable without destruction of the growing peptide chain or racemization of any of the chiral centers contained therein. Suitable protecting groups are t-butyloxycarbonyl (Boc), benzyloxycarbonyl (Cbz), biphenylisopropyloxycarbonyl, t-amyloxycarbonyl, isobornyloxycarbonyl, $\alpha,\alpha$-dimethyl-3,5-dimethoxybenzyloxycarbonyl, o-nitrophenylsulfenyl, 2-cyano-t-butyloxycarbonyl, 9-fluoroenylmethyloxycarbonyl and the like, especially t-butyloxycarbonyl (Boc).

Particularly preferred side chain protecting groups are, for arginine:nitro, p-toluenesulfonyl, 4-methoxybenzenesulfonyl, Cbz, Boc and adamantyloxycarbonyl; for tyrosine:benzyl, o-bromobenzyloxycarbonyl, 2,6-dichlorobenzyl, isopropyl, cyclohexyl, cyclopentyl and acetyl; for serine:benzyl and tetrahydropyranyl; for histidine:benzyl, p-toluenesulfonyl and 2,4-dinitrophenyl.

The C-terminal amino acid is attached to a suitable solid support. Suitable solid supports useful for the above synthesis are those materials which are inert to the reagents and reaction conditions of the stepwise condensation-deprotection reactions, as well as being insoluble in the media used. Suitable solid supports are chloromethylpolystyrene-divinylbenzene polymer, hydroxymethyl-polystyrene-divinylbenzene polymer, and the like, especially chloromethyl-polystyrene-1% divinylbenzene polymer. For the special case where the C-terminus of the compound will be glycinamide, a particularly useful support is the benzhydrylamino-polystyrene-divinylbenzene polymer described by P. Rivaille, et al, *Helv. Chim. Acta.*, 54, 2772 (1971). The attachment to the chloromethyl polystyrene-divinylbenzene type of resin is made by means of the reaction of the $N^\alpha$-protected amino acid, especially the Boc-amino acid, as its cesium, tetramethylammonium, triethylammonium, 4,5-diazabicyclo[5.4.0]undec-5-ene, or similar salt in ethanol, acetonitrile, N,N-dimethylformamide (DMF), and the like, especially the cesium salt in DMF, with the chloromethyl resin at an elevated temperature, for example between about 40° and 60° C., preferably about 50° C., for from about 12 to 48 hours, preferably about 24 hours. The $N^\alpha$-Boc-amino acid is attached to the benzhydrylamine resin by means of an N,N'-dicyclohexylcarbodiimide (DCC)/1-hydroxybenzotriazole (HBT) mediated coupling for from about 2 to about 24 hours, preferably about 12 hours at a temperature of between about 10° and 50° C., preferably 25° C. in a solvent such as dichloromethane or DMF, preferably dichlormethane. The coupling of successive protected amino acids can be carried out in an automatic polypeptide synthesizer as is well known in the art. The removal of the $N^\alpha$-protecting groups may be performed in the presence of, for example, a solution of trifluoroacetic acid in methylene chloride, hydrogen chloride in dioxane, hydrogen chloride in acetic acid, or other strong acid solution, preferably 50% trifluoroacetic acid in dichloromethane at about ambient temperature. Each protected amino acid is preferably introduced in approximately 2.5 molar excess and the coupling may be carried out in dichloromethane, dichloromethane/DMF mixtures, DMF and the like, especially in methylene chloride at about ambient temperature. The coupling agent is normally DCC in dichloromethane but may be N,N'-di-iso-propylcarbodimide or other carbodimide either alone or in the presence of HBT, N-hydroxysuccinimide, other N-hydroxyimides or oximes. Alternately, protected amino acid active esters (e.g. p-nitrophenyl, pentafluorophenyl and the like) or symmetrical anhydrides may be used.

At the end of the solid phase synthesis the fully protected polypeptide is removed from the resin. When the linkage to the resin support is of the benzyl ester type, cleavage is by means of aminolysis with an alkylamine or fluoroalkylamine for peptides with a proline C-terminus, or by aminolysis with, for example, ammonia/methanol or ammonia/ethanol for peptides with a glycine C-terminus at a temperature between about 10° and 50° C., preferably about 25° C., for between about 12 and 24 hours preferably about 18 hours. Alternatively, the peptide may be removed from the resin by transesterification, e.g., with methanol, followed by aminolysis. The protected peptide may be purified at this point by silica gel chromatography. The removal of the (side chain) protecting groups from the polypeptide is performed by treating the aminolysis product with, for example, anhydrous liquid hydrogen fluoride in the presence of anisole or other carbonium ion scavenger, treatment with hydrogen fluoride/pyridine complex, treatment with tris(trifluoroacetyl)boron and trifluoroacetic acid, by reduction with hydrogen and palladium on carbon or polyvinylpyrrolidone, or by reduction with sodium in liquid ammonia, preferably with liquid hydrogen fluoride, and anisole at a temperature between about $-10°$ and $+10°$ C., preferably about 0° C., for between about 15 minutes and 1 hour, preferably about 30 minutes. For the glycine terminal peptides on the benzhydrylamine resins, the resin cleavage and deprotection steps may be combined in a single step utilizing liquid hydrogen fluoride and anisole as described above. The fully deprotected polypeptide is then purified by a sequence of chromatographic steps employing any or all of the following types: ion exchange on a weakly basic resin in the acetate form; hydrophobic adsorption chromatography on underivatized polystyrene-divinylbenzene (for example Amberlite XAD); silica gel adsorption chromatography; ion exchange chromatography on carboxymethylcellulose; partition chromatography, e.g. on Sephadex G-25, or countercurrent distribution; high performance liquid chromatography (HPLC), especially reverse phase HPLC on octyl- or octadecylsilyl-silica bonded phase column packing.

If a racemic amino acid is used in the 6-position, the diastereomeric nonapeptide or decapeptide final products are separated, and the desired peptide containing a D-amino acid in the 6-position is isolated and purified, preferably during the above-described chromatographic process.

The preparation of peptides having C-terminal azaglycine amides is preferably done using classical peptide solution synthesis using known peptide intermediates. This is described in more detail in Example 3.

Thus, in another aspect the present invention relates to a method for preparing compounds of the formula (I) which process comprises:

(i) removing protecting groups and, optionally, covalently bound solid support from a protected polypeptide to afford a compound of Formula (I) or a salt thereof, and optionally (ii) converting a compound of Formula (I) to a pharmaceutically acceptable salt thereof, or (iii) converting a salt of a compound of Formula (I) to a pharmaceutically acceptable salt thereof, or (iv) decomposing a salt of a compound of Formula (I) to a free polypeptide of Formula (I).

The following examples are given to enable those skilled in the art to more fully understand and practice the present invention. They should not be construed as a limitation upon the scope of the invention, but merely as being illustrative and representative thereof.

PREPARATION A

A solution of 26.7 g of N-carbobenzyloxy-D-aspartic acid in 60 ml of anhydrous tetrahydrofuran and a solution of 22.8 g of dicyclohexylcarbodiimide in 60 ml of anhydrous tetrahydrofuran are cooled in separate flasks to $-5°$ C. and then mixed. After 6 hours of stirring with the temperature controlled between 0° and 5° C., the dicyclohexylurea that precipitated is filtered, and the filtrate is evaporated to dryness using reduced pressure. The pale yellow powder which is produced is dissolved in 70 ml of anhydrous tetrahydrofuran and heated with 10.4 ml of dry benzyl alcohol and stirred at room temperature for 24 hours. To this solution is added 0.5 ml of acetic acid, then the dicyclohexylurea precipitate produced is removed by filtration. The solvent is removed in vacuo leaving a yellow oil which is dissolved in 120 ml of diethyl ether and treated with 27.3 g of dicyclohexylamine. After cooling and scratching of the flask to initiate precipitation, white crystals are formed, which are filtered, washed with ether and dried to yield 32 g of the dicyclohexylamine salt.

The crude salt is redissolved in 250 ml of ethyl acetate to which is subsequently added a solution containing 40 g of citric acid in 200 ml of water. The heterogeneous mixture is stirred vigorously for 0.5 hours. The organic layer is separated and dried over anhydrous magnesium sulfate. The magnesium sulfate is removed by filtration and the filtrate is removed in vacuo to produce an oil which is redissolved in ethyl acetate. Hexane is added to the cloud point. After cooling the mechanical initiation of precipitation, crystals are formed which are filtered, washed with ether and dried in vacuo to yield 11.7 g of pure α-benzyl N$^\alpha$-carbobenzyloxy-D-aspartate having a melting point of 92°–96° C., $[\alpha]_D^{25} + 9.7°$ (C 1, HOAc).

PREPARATION B

A solution of 5.72 g of α-benzyl N$^\alpha$-benzyloxycarbonyl-D-aspartate in 50 ml of anhydrous tetrahydrofuran is cooled to $-20°$ C. and treated with 2.22 ml of triethylamine and 2.08 ml of iso-butylchloroformate. After ten minutes of stirring at $-10°$ C. a solution of 1.91 g of 1,2-phenylenediamine in 30 ml of tetrahydrofuran is added to the reaction mixture and stirring is continued for 1.5 hours as the temperature of the solution rose to 25° C. The solution is poured into 500 ml of a 5% solution of sodium bicarbonate, and the resulting precipitate is filtered, dried in vacuo, dissolved in 150 ml of glacial acetic acid and heated at 60° C. for 1.5 hours. The solvent is removed in vacuo and the residue is further dried by an azeotropic distillation under reduced pressure using three 100 ml portions of p-dioxane. The crude product is purified by column chromatography using silicic acid as a solid phase and eluted using a solvent gradient of increasing polarity from 100% dichloromethane to a 50/50 mixture of dichloromethane/diethyl ether. Thin layer chromatography is used to analyze the fractions. The product is identified, collected, concentrated to an oil in vacuo, and crystallized from ethyl acetate/hexane to yield 2.75 g of benzyl $N^\alpha$-benzyloxycarbonyl-3-(2-benzimidazolyl)-D-alanate, m.p. 136°-8°, $[\alpha]_D^{25}$ 15.8° (C 1, MeOH).

Repeating the above procedure, substituting a stoichiometrically equivalent of
4-methyl-1,2-diaminobenzene,
4,5-dimethyl-1,2-diaminobenzene,
4-chloro-1,2-diaminobenzene,
4,5-dichloro-1,2-diaminobenzene,
4-bromo-1,2-diaminobenzene,
4-butyl-1,2-diaminobenzene,
1,2-diaminonaphthalene,
2,3-diaminonaphthalene,
6-chloro-1,2-diaminonaphthalene,
6-butyl-1,2-diaminonaphthalene,
2,3-diamino-6-methylnaphthalene,
2,3-diamino-6,7-dimethylnaphthalene,
2,3-diamino-6-chloronaphthalene,
2,3-diamino-6,7-dichloronaphthalene,
2,3-diamino-6-bromonaphthalene,
2,3-diamino-6-butylnaphthalene,
2-hydroxyaniline,
5-methyl-2-hydroxyaniline,
4,5-dimethyl-2-hydroxyaniline,
5-chloro-2-hydroxyaniline,
4,5-dichloro-2-hydroxyaniline,
5-bromo-2-hydroxyaniline,
5-butyl-2-hydroxyaniline,
2-aminothiophenol,
4-methyl-2-aminothiophenol,
4,5-dimethyl-2-aminothiophenol,
5-chloro-2-aminothiophenol,
4,5-dichloro-2-aminothiophenol,
2-amino-1-thionaphthol,
4-bromo-2-aminothiophenol,
4-butyl-2-aminothiophenol,
2-amino-1-naphthol,
3-amino-2-naphthol,
6-methyl-2-amino-1-naphthol,
6,7-dimethyl-2-amino-1-naphthol,
6-methyl-3-amino-2-naphthol,
6,7-dimethyl-3-amino-2-naphthol,
6-chloro-3-amino-2-naphthol, and
6,7-dichloro-3-amino-2-naphthol
for 1,2-phenylenediamine, there are obtained the following benzyl $N^\alpha$-benzyloxycarbonyl (Cbz) protected amino acids Benzyl $N^\alpha$-Cbz-3-[2-(5-methylbenzimidazolyl)]-D-alanate,
Benzyl $N^\alpha$-Cbz-3-[2-(5,6-dimethylbenzimidazolyl)]-D-alanate,
Benzyl $N^\alpha$-Cbz-3-[2-(5-chlorobenzimidazolyl)]-D-alanate,
Benzyl $N^\alpha$-Cbz-3-[2-(5,6-dichlorobenzimidazolyl)]-D-alanate,
Benzyl $N^\alpha$-Cbz-3-[2-(5-bromobenzimidazolyl)]-D-alanate,
Benzyl $N^\alpha$-Cbz-3-[2-(5-butylbenzimidazolyl)]-D-alanate,
Benzyl $N^\alpha$-Cbz-3-[2-(naphth[1,2-d]imidazolyl)]-D-alanate,
Benzyl $N^\alpha$-Cbz-3-[2-(naphth[2,3-d]imidazolyl)]-D-alanate (Structure identified by proton magnetic resonance spectroscopy,)
Benzyl $N^\alpha$-Cbz-3-[2-(7-chloronaphth[1,2-d]imidazolyl)]-D-alanate,
Benzyl $N^\alpha$-Cbz-3-[2-(7-butylnaphth[1,2-d]-imidazolyl)]-D-alanate,
Benzyl $N^\alpha$-Cbz-3-[2-(6-methylnaphth[2,3-d]imidazolyl)]-D-alanate,
Benzyl $N^\alpha$-Cbz-3-[2-(6,7-dimethylnaphth[2,3-d]imidazolyl)]-D-alanate,
Benzyl $N^\alpha$-Cbz-3-[2-(6-chloronaphth[2,3-d]imidazolyl)]-D-alanate,
Benzyl $N^\alpha$-Cbz-3-[2-(6,7-dichloronaphth[2,3-d]imidazolyl)]-D-alanate,
Benzyl $N^\alpha$-Cbz-3-[2-(6-bromonaphth[2,3-d]imidazolyl)]-D-alanate,
Benzyl $N^\alpha$-Cbz-3-[2-(6-butylnaphtho[2,3-d]imidazolyl)]-D-alanate,
Benzyl $N^\alpha$-Cbz-3-(2-benzoxazolyl)-D-alanate,
Benzyl $N^\alpha$-Cbz-3-[2-(5-methylbenzoxazolyl)]-D-alanate,
Benzyl $N^\alpha$-Cbz-3-[2-(5,6-dimethylbenzoxazolyl)]-D-alanate,
Benzyl $N^\alpha$-Cbz-3-[2-(5-chlorobenzoxazolyl)]-D-alanate,
Benzyl $N^\alpha$-Cbz-3-[2-(5,6-dichlorobenzoxazolyl)]-D-alanate,
Benzyl $N^\alpha$-Cbz-3-[2-(5-bromobenzoxazolyl)]-D-alanate,
Benzyl $N^\alpha$-Cbz-3-[2-(5-butylbenzoxazolyl)]-D-alanate,
Benzyl $N^\alpha$-Cbz-3-(2-benzothiazolyl)-D-alanate, m.p. 74°-75°, $[\alpha]_D^{25}$ 33.9° (C 1, MeOH),
Benzyl $N^\alpha$-Cbz-3-[2-(5-methylbenzothiazolyl)]-D-alanate,
Benzyl $N^\alpha$-Cbz-3-[2-(5,6-dimethylbenzothiazolyl)]-D-alanate,
Benzyl $N^\alpha$-Cbz-3-[2-(5-chlorobenzothiazolyl)]-D-alanate,
Benzyl $N^\alpha$-Cbz-3-[2-(5,6-dichlorobenzothiazolyl)]-D-alanate,
Benzyl $N^\alpha$-Cbz-3-(2-naphtho[2,1-d]thiazolyl)-D-alanate,
Benzyl $N^\alpha$-Cbz-3-[2-(5-bromobenzothiazolyl)]-D-alanate,
Benzyl $N^\alpha$-Cbz-3-[2-(5-butylbenzothiazolyl)]-D-alanate,
Benzyl-$N^\alpha$-Cbz-3-(2-naphth[2,1-d]oxazolyl)-D-alanate,
Benzyl-$N^\alpha$-Cbz-3-(2-naphth[2,3-d]oxazolyl)-D-alanate,
Benzyl-$N^\alpha$-Cbz-3-[2-(7-methylnaphth[2,1-d]-oxazolyl)]-D-alanate,
Benzyl-$N^\alpha$-Cbz-3-[2-(7,8-dimethylnaphth[2,1-d]-oxazolyl)]-D-alanate,
Benzyl-$N^\alpha$-Cbz-3-[2-(6-methylnaphth[2,3-d]-oxazolyl)]-D-alanate,
Benzyl-$N^\alpha$-Cbz-3-[2-(6,7-dimethylnaphth[2,3-d]-oxazolyl)]-D-alanate,
Benzyl-$N^\alpha$-Cbz-3-[2-(6-chloronaphth[2,3-d] oxazolyl)]-D-alanate, and
Benzyl-$N^\alpha$-Cbz-3-[2-(6,7-dichloronaphth[2,3-d]-oxazolyl)]-D-alanate.

PREPARATION C

Alternatively, the sulfur containing derivatives described in Preparation B may also be prepared according to the following method:

A 10.7 g portion of α-benzyl N$^α$-benzyloxycarbonyl-D-aspartate is converted to the corresponding acid chloride by treatment in 200 ml of dry ether at 0° C. with 6.9 g of phosphorus pentachloride. After 15 minutes the solvent is evaporated and the residue is filtered to yield 9.2 g of crystalline product of m.p. 69°–72°. A 2.8 g portion of this β-acid chloride is added to a solution of 0.9 g of the disulfide of o-aminothiophenol in 75 ml of tetrahydrofuran and 1.3 ml of diisopropylethylamine. The solution is stirred at 0° for 4 hours, the solvent is evaporated, and the residue is suspended in ethanol. The solid is filtered to yield 2.6 g of the disulfide of α-benzyl N$^α$-benzyloxycarbonyl-D-aspartate β-(o-thioanalide) of m.p. 182°–185°, $[α]_D^{25}$ 13.3° (C 1, DMF).

A 2.2 g portion of this disulfide is reduced to the sulfide by treatment with 5.5 g of zinc powder in 3 portions in 200 ml of glacial acetic acid at 50° C. After 3 hours the zinc powder is filtered and the solvent is evaporated. The residual traces of acetic acid are removed by addition of 200 ml of dioxane and re-evaporation to dryness. The residue, consisting of essentially pure α-benzyl N$^α$-benzyloxycarbonyl-D-aspartate p-(o-thioanalide), is cyclized by treatment in 200 ml of dioxane and 2.5 ml of triethylamine. The solution is stirred under nitrogen gas for 20 hours, the solvent is evaporated and the residue is purified using preparative thin layer chromatography on silicic acid. The plates are developed using methylene chloride/diethyl ether (15:1) and the major ultraviolet absorbing band is removed. The product is recovered from the silicic acid by washing with the development solvent, and is crystallized from ethyl acetate/hexane to yield 1.5 g of a white, crysalline solid; α-benzyl N$^α$-benzyloxycarbonyl-3-(2-benzothiazoly)-D-alaninate of m.p. 74°–75° $[α]_D^{25}$ 33.9° (C 1, methanol).

Hydrogenation at atmospheric pressure of 1.25 g of this protected material in 100 ml of glacial acetic acid in the presence of 500 mg of 10% palladium on carbon completely removed the benzyl ester but only partially removed the benzyloxycarbonyl protecting group. The catalyst is then filtered on a celite pad and the solvent was removed at reduced pressure. The residue is treated with 75 ml of 4 N hydrogen bromide gas in glacial acetic acid for 2 hours. The solvent is removed and the last traces of acetic acid are removed by co-evaporation with three portions of dioxane to give 1.0 g of crude 3-(2-benzothiazolyl)-D-alanine.

This crude residue is directly treated with 1.4 g of di-t-butyldicarbonate in 50 ml of 50% dioxane/water at pH 9.5. The pH is maintained at 9.5 by additions of 0.5 N sodium hydroxide solution for 3 hours. The reaction mixture is washed with ether, brought to pH 2.5 with sodium bisulfate, and extracted with ethyl acetate. The ethyl acetate extract is dried over magnesium sulfate, filtered, and concentrated. Crystallization from ethyl acetate/hexane yields 0.54 g of white, crystalline N$^α$-t-butyloxycarbonyl-2-(2-benzothiazolyl)-D-alanine of m.p. 148°–150° C., $[α]_D^{25}$ +8.4° (C 1, methanol).

PREPARATION D

A solution comprised of 3.87 g of benzyl N$^α$-benzyloxycarbonyl-3-(2-benzimidazolyl)-D-alanate and 2.3 ml of 2,6-lutidine in 100 ml of dimethylsulfoxide is treated with 3.92 g of di-t-butyldicarbonate. After stirring at room temperature for 1.5 hours, 1.15 ml of 2,6-lutidine and 1.96 g of di-t-butyldicarbonate are added. After 4 more hours, another 1.15 ml of 2,6-lutidine and 1.96 g of di-t-butyldicarbonate are added. After 20 hours of reaction, the mixture is partitioned between water and ethyl acetate. The ethyl acetate layer is dried using magnesium sulfate, filtered, and evaporated to dryness. The residue is purified by column chromatography using silicic acid as the solid phase and an eluent which is a gradient from 100% dichloromethane to 25/75 diethyl ether/dichloromethane. Thin layer chromatography is used to analyze the product which is then collected and concentrated to yield 4.6 g of benzyl N$^α$-benzyloxycarbonyl-N$^{im}$-t-butyloxycarbonyl-3-(2-benzimidazolyl)-D-alanate as an oil.

PREPARATION E

A solution of 4.0 g of benzyl N$^α$-benzyloxycarbonyl-N$^{im}$-t-butyloxycarbonyl-3-(2-benzimidazolyl)-D-alanate and 15.2 g of di-t-butyldicarbonate in 150 ml of absolute ethanol is stirred with 1.0 g of 10% palladium on carbon under a hydrogen atmosphere at atmospheric pressure and room temperature. After hydrogen consumption ceases after 2.5 hours, the catalyst is filtered and washed with absolute ethanol. The filtrate is evaporated to dryness in vacuo. The residue is suspended in 100 ml of 50/50 dioxane/water, treated with 1.8 g of di-t-butyldicarbonate and the pH of the solution is adjusted to 9.5 using 0.5 normal sodium hydroxide. After stirring for 18 hours at this pH level, the solution is evaporated to dryness, and the residue is partitioned between aqueous sodium bisulfate at a pH level of 2.5 and ethyl acetate. The ethyl acetate layer is dried using magnesium sulfate and filtered. The filtrate is dried to give 1.4 g of an off-white solid which is purified by recrystallization from ethyl acetate/hexane and gives 0.64 g of N$^α$,N$^{im}$-di-t-butyloxycarbonyl-3-(2-benzimidazolyl)-D-alanine, m.p. 160°–161° C., $[α]_{25}^D$ +21.7° (C 1, methanol).

PREPARATION F

A solution of 2.64 g of benzyl N$^α$-benzyloxycarbonyl-3-(2-benzimidazolyl)-D-alanate in 70 ml of glacial acetic acid is treated with 0.4 g of 10% palladium on carbon and stirred under hydrogen at atmospheric pressure for 1 hour. The solution is filtered using diatomaceous earth and the filtrate is concentrated in vacuo to an oil. The residue is dried using azeotropic distillation by treatment with two portions of 30 ml of p-dioxane in vacuo.

The product is recrystallized from methanol/diethyl ether to give 3-(2-benzimidazolyl)-D-alanine containing 0.5 molecules of methanol of crystallization, m.p. 198° C. with decomposition), $[α]_D^{25}$ −11.6° (C 0.2, acetic acid).

PREPARATION G

A solution of 1.44 g of 3-(2-benzimidazolyl)-D-alanine in 250 ml of 2 normal hydrochloric acid and 0.5 g of platinum oxide catalyst is added. The mixture is stirred under hydrogen at atmospheric pressure while aliquots are removed and analyzed by ultraviolet spectroscopy to monitor the progress of the reaction. After 22 hours no starting alanine derivative remain, the mixture is filtered through diatomaceous earth, and the filtrate is reduced to dryness giving a yellow oil. The oil is purified using ion exchange chromatography with DOWEX AG-50 as the solid support and eluent gradients from water to 1 Molar ammonium hydroxide followed by a gradient of 1 Molar ammonium hydroxide to 2 Molar ammonium hydroxide. The product in the eluent fractions is analyzed using thin layer chromatography. The product is collected, concentrated in vacuo, and lyophilized from water to give 1.19 g of 3-[2-(4,5,6,7-tetrahydrobenzimidazolyl)]-D-alanine, m.p. 134°–140° C., $[\alpha]_D^{25}$ −15.9° (C 0.6, acetic acid).

Repeating the above procedure substituting a stoichiometrically equivalent of 3-(5-methyl-2-benzimidazolyl)-D-alanine,
3-(5,6-dimethyl-2-benzimidazolyl)-D-alanine,
3-(5-chloro-2-benzimidazolyl)-D-alanine,
3-(5,6-dichloro-2-benzimidazolyl)-D-alanine,
3-(5-bromo-2-benzimidazolyl)-D-alanine,
3-(5-butyl-2-benzimidazolyl)-D-alanine,
3-(2-benzothiazolyl)-D-alanine,
3-(5-methyl-2-benzothiazolyl)-D-alanine,
3-(5,6-dimethyl-2-benzothiazolyl)-D-alanine,
3-(5-chloro-2-benzothiazolyl)-D-alanine,
3-(5,6-dichloro-2-benzothiazolyl)-D-alanine,
3-(2-benzoxazolyl)-D-alanine,
3-(5-methyl-2-benzoxazolyl)-D-alanine,
3-(5,6-dimethyl-2-benzoxazolyl)-D-alanine,
3-(5-chloro-2-benzoxazolyl)-D-alanine,
3-(5,6-dichloro-2-benzoxazolyl)-D-alanine,
3-(2-naphth[1,2-d]imidazolyl)-D-alanine,
3-(7-bromo-2-naphth[1,2-d]imidazolyl)-D-alanine,
3-(7-butyl-2-naphth[1,2-d]imidazolyl)-D-alanine,
3-(2-naphth[2,3-d]imidazolyl)-D-alanine,
3-[2-(6-methylnaphth[2,3-d]imidazolyl)]-D-alanine,
3-[2-(6-chloronaphth[2,3-d]imidazolyl)]-D-alanine,
3-(6-bromo-2-naphth[2,3-d]imidazolyl)-D-alanine,
3-(6-butyl-2-naphth[2,3-d]imidazolyl)-D-alanine,
3-(2-naphtho[2,3-d]thiazolyl)-D-alanine,
3-(2-naphtho[2,1-d]thiazolyl)]-D-alanine,
3-[2-(6-methylnaphtho[2,3-d]thiazolyl)]-D-alanine,
3-[2-(6-chloronaphtho[2,3-d]thiazolyl)-D-alanine,
3-(2-naphth[2,1-d]oxazolyl)-D-alanine,
3-(2-naphth[2,3-d]oxazolyl)-D-alanine,
3-[2-(6-methylnaphth[2,3-d]oxazolyl)]-D-alanine, and
3-[2-(6-chloronaphth[2,3-d]oxazolyl)]-D-alanine
for 3-(2-benzimidazolyl)-D-alanine, there are obtained the following amino acids 3-[2-(5-methyl-4,5,6,7-tetrahydrobenzimidazolyl)]-D-alanine,
3-[2-(5,6-dimethyl-4,5,6,7-tetrahydrobenzimidazolyl)]-D-alanine,
3-[2-(5-chloro-4,5,6,7-tetrahydrobenzimidazolyl)]-D-alanine,
3-[2-(5,6-dichloro-4,5,6,7-tetrahydrobenzimidazolyl)]-D-alanine,
3-(2-(5-bromo-4,5,6,7-tetrahydrobenzimidazolyl)]-D-alanine,
3-(2-(5-butyl-4,5,6,7-tetrahydrobenzimidazolyl)]-D-alanine,
3-[2-(4,5,6,7-tetrahydrobenzothiazolyl)]-D-alanine,
3-[2-(5-methyl-4,5,6,7-tetrahydrobenzothiazolyl)]-D-alanine,
3-[2-(5,6-dimethyl-4,5,6,7-tetrahydrobenzothiazolyl)]-D-alanine,
3-[2-(5-chloro-4,5,6,7-tetrahydrobenzothiazolyl)]-D-alanine,
3-[2-(5,6-dichloro-4,5,6,7-tetrahydrobenzothiazolyl)]-D-alanine,
3-[2-(4,5,6,7-tetrahydrobenzoxazolyl)]-D-alanine,
3-[2-(5-methyl-4,5,6,7-tetrahydrobenzoxazolyl)]-D-alanine,
3-[2-(5,6-dimethyl-4,5,6,7-tetrahydrobenzoxazolyl)]-D-alanine,
3-[2-(5-chloro-4,5,6,7-tetrahydrobenzoxazolyl)]-D-alanine,
3-[2-(5,6-dichloro-4,5,6,7-tetrahydrobenzoxazolyl)]-D-alanine,
3-[2-(4,5,5a,6,7,8,9,9a-octohydronaphth[1,2-d]-imidazolyl)]-D-alanine,
3-[2-(7-bromo-4,5,5a,6,7,8,9,9a-octohydronaphth-[1,2-d]-imidazolyl)]-D-alanine,
3-[2-(7-butyl-4,5,5a,6,7,8,9,9a-octohydronaphth-[1,2-d]-imidazolyl)]-D-alanine,
3-[2-(4,4a,5,6,7,8,8a,9-octohydronaphtho[2,3-d]-imidazolyl)]-D-alanine,
3-[2-(6-methyl-4,4a,5,6,7,8,8a,9-octohydronaphth-[2,3-d]imidazolyl)]-D-alanine,
3-[2-(6-chloro-4,4a,5,6,7,8,8a,9-octohydronaphth-[2,3-d]imidazolyl)]-D-alanine,
3-[2-(6-bromo-4,4a,5,6,7,8,8a,9-octohydronaphth-[2,3-d]-imidazolyl)]-D-alanine,
3-[2-(6l -butyl-4,4a,5,6,7,8,8a,9-octohydronaphth-[2,3-d]-imidazolyl)]-D-alanine,
3-[2-(4,4a,5,6,7,8,8a,9-octohydronaphtho[2,3-d]-thiazolyl)]-D-alanine,
3-[2-(4,4a,5,6,7,8,8a,9-octohydronaphtho[2,1-d]-thiazolyl)]-D-alanine,
3-[2-(6-methyl-4,4a,5,6,7,8,8a,9-octohydronaphtho-[2,3-d]thiazolyl)]-D-alanine,
3-[2-(6-chloro-4,4a,5,6,7,8,8a,9-octohydronaphtho-[2,3-d]thiazolyl)]-D-alanine,
3-[2-(4,5,5a,6,7,8,9,9a-octohydronaphth-[2,1-d]oxazolyl)]-D-alanine,
3-[2-(4,4a,5,6,7,8,8a,9-octohydronaphth-[2,3-d]oxazolyl)]-D-alanine,
3-[2-(6-methyl-4,4a,5,6,7,8,8a,9-octohydronaphth-[2,3-d]-oxazolyl)]-D-alanine, and
3-[2-(6-chloro-4,4a,5,6,7,8,8a,9-octohydronaphth-[2,3-d]oxazolyl)]-D-alanine, respectively.

PREPARATION H

A solution of 0.90 g of 3-[2-(4,5,6,7-tetrahydrobenzimidazolyl)]-D-alanine in 25 ml of 50/50 dioxane/water is treated with 1.03 g of di-t-butyldicarbonate. The pH is maintained at 8.7 by means of automatic titration with 0.5 M NaOH by a Radiometer pH stat. Each one-half hour, an additional 1.03 g of di-t-butyldicarbonate is added until a total of 6.18 g is added. The reaction is then stirred at pH 8.7 and room temperature overnight. After 20 hours of stirring, 1.03 g of di-t-butyldicarbonate is added, and the pH of the solution is raised to 9.5 for 2 hours. The solution is evaporated to dryness, the residue is taken up in 200 ml of aqueous sodium bisulfate having a pH of 2.5 and the resulting solution is extracted with ethyl acetate. The ethyl acetate extract is dried using magnesium sulfate, filtered, and evaporated to give an oil which is crystallized from ethyl acetate to yield 0.36 g of $N^\alpha$, $N^{im}$-di-t-butyloxycarbonyl-3-[2-(4,5,6,7-tetrahydrobenzimidazolyl)]-D-alanine, m.p. 164°–170° C.

Repeating the above procedure substituting a stoichiometric equivalent of each of the compounds prepared according to Preparation G above for 3-[2-(4,5,6,7-tetrahydrobenzimidazolyl)]-D-alanine, there are obtained the appropriately protected $N^\alpha$-$N^{im}$-di-t-butyloxycarbonyl-D-alanine derivatives.

EXAMPLE 1

In the reaction vessel of a Beckman 990 Peptide Synthesizer is placed 1.09 g (1.0 mmol) of benzhydrylamino-polystyrene-divinylbenzene resin (Lab Systems, Inc.) as described by Rivaille, supra. Amino acids are added sequentially to this resin by means of a synthesis program, as follows:

| Step | | | |
|---|---|---|---|
| 1 | $CH_2Cl_2$ wash | 1 time | 1.5 min |
| 2 | 50% $CF_3CO_2H/CH_2Cl_2$—deprotection | 1 time | 1.5 min |
| 3 | 50% $CF_3CO_2H/CH_2Cl_2$—deprotection | 1 time | 30 min |
| 4 | $CH_2Cl_2$ wash | 3 times | 1.5 min |
| 5 | 10% triethylamine/$CH_2Cl_2$ | 2 times | 1.5 min |
| 6 | $CH_2Cl_2$ wash | 3 times | 1.5 min |
| 7 | $N^\alpha$-Boc-amino acid solution | 1 time | add |
| 8 | N,N'-dicyclohexylcarbodiimide solution | 1 time | add |
| 9 | $CH_2Cl_2$ rinse and hold coupling | 1 time | coupling reaction 2 hr |
| 10 | $CH_2Cl_2$—rinse add | 1 time | 1.5 min |
| 11 | $CH_2Cl_2$ wash | 3 times | 1.5 min |
| 12 | ethanol wash | 3 times | 1.5 min |
| 13 | $CH_2Cl_2$ wash | 3 times | 1.5 min |

Steps 1–13 complete a coupling cycle for one amino acid and completeness of the reaction is checked by the ninhydrin method of E. Kaiser, et al., *Anal. Biochem.*, 34, 595 (1970).

The resin is coupled sequentially with a 2.5 molar excess of each protected amino acid and DCC. Thus, the resin is treated during successive coupling cycles with 0.438 g Boc-Gly-OH, and 0.405 g 1-hydroxybenzotriazole
0.538 g Boc-Pro-OH,
1.10 g iso-Amyloxycarbonyl-Arg(Tosyl)-OH,
0.623 g Boc-Leu-OH,
0.763 g $N^\alpha$-Boc-3-(2-benzimidazolyl)-D-alanine and 0.405 g 1-hydroxybenzotriazole,
1.24 g N-Boc,O-2-bromobenzoyloxycarbonyl-L-tyrosine,
0.74 g Boc-Ser(Benzyl)-OH,
0.76 g $N^\alpha$-Boc-Trp-OH,
1.02 g Boc-His(Tosyl)-OH,
0.405 g 1-hydroxybenzotriazole, and
0.32 g pyroglutamic acid.

The resin is removed from the reaction vessel, washed with $CH_2Cl_2$, and dried in vacuo to yield 1.5 g of protected polypeptide resin.

The polypeptide product is simultaneously removed from the resin and completely deprotected by treatment with anhydrous liquid HF. A mixture of 1.5 g of protected polypeptide resin and 2 ml of anisole (scavenger) in a Kel-F reaction vessel is treated with 30 ml of redistilled (from $CoF_3$) anhydrous liquid HF at 0° C. for 30 minutes. The HF is evaporated under vacuum and the residue of (pyro)-Glu-His-Trp-Ser-Tyr-3-(2-benzimidazolyl)-D-alanyl-Leu-Arg-Pro-Gly-$NH_2$, as its HF salt, is washed with ether. The residue is then extracted with glacial acetic acid. The acetic acid extract is lyophilized to yield 0.4 g of crude material.

The crude polypeptide is loaded on a 4×40 cm. Amberlite XAD-4 column (polystyrene-4% divinylbenzene copolymer) and eluted with a concave gradient from water (0.5 l) to ethanol (1 l). The tubes containing fractions from effluent volume 500 ml to 1,100 ml are pooled and stripped to dryness to yield 400 mg of partially purified polypeptide.

Final purification is achieved by preparative high performance liquid chromatography on a 20–30 mg sample using a 0.9×550 mm column of 40–50µ octadecylsilated silica (Merck Lichroprep $C_{18}$). The eluent is 64% 0.03 M $NA_4OAc$/30–36% acetonitrile. In 3 to 4 runs a total of about 60 mg of crude material is purified. After three lyophilizations from water, 15–20 mg of pure (pyro)-glutamyl-histidyl-tryptophyl-seryl-tyrosyl-3-(2-benzimidazolyl)-D-alanyl-leucyl-arginyl-proline ethylamide is obtained as its acetic acid addition salt.

EXAMPLE 2

For the synthesis of analogues with a C-terminal Pro-$NHCH_2CH_3$, a synthesis program identical to that described in Example 1 is used. The Beckman 990 Synthesizer reaction vessel is loaded with 2.13 g of Boc-Pro-O-Resin, prepared by the reaction of equimolar ratios of the dry cesium salt of Boc-Pro-OH with chloromethyl-polystyrene/1% divinylbenzene (Lab Systems, Inc.). The quantity of Boc-Pro-O-Resin taken contains 1.4 mmol of proline.

The resin is coupled sequentially with a 2.5 molar excess of each protected amino acid and DCC. Thus, the resin is reacted during successive coupling cycles with
0.55 g $N^\alpha$-iso-Amyloxycarbonyl-Arg(Tosyl)-OH,
0.31 g Boc-Leu-OH $H_2O$,
0.50 g $N^\alpha$-$N^{im}$-Di-Boc-3-(2-benzimidazolyl)-D-alanine and 0.22 g of 1-hydroxybenzotriazole,
0.62 g N-Boc-O-2-bromobenzyloxycarbonyl-L-tyrosine, and 0.22 g 1-hydroxybenzotriazole,
0.37 g Boc-Ser(Benzyl)-OH followed by a second coupling with 0.22 g of Boc-Ser(Benzyl)-OH, then coupled twice with
0.38 g Boc-Trp-OH, coupled twice with
0.51 g Boc-His(Tosyl)-OH, and 0.22 g of 1-Hydroxybenzotriazole, and coupled twice with
0.16 g pyroglutamic acid.

The resin is removed from the reaction vessel, washed with $CH_2Cl_2$, and dried in vacuo to yield 1.37 g of protected polypeptide resin.

The protected polypeptide is cleaved from the resin by aminolysis with 20 ml of ethylamine for 20 hours at 4° C. The ethylamine is allowed to evaporate and the resin is extracted with methanol. The methanol is evaporated to yield 1.10 g of pyro-Glu-His(Tosyl)-Trp-Ser(Benzyl)-Tyr(2-bromobenzyloxycarbonyl)-3-(2-benzimidazolyl)-D-alanyl-Leu-Arg(Tosyl)-Pro-NH-$CH_2CH_3$.

The crude polypeptide is deprotected by treatment with a mixture of 2 ml anisole and 25 ml redistilled (from $CoF_3$) anhydrous liquid HF at 0° C. for 30 minutes in a Kel-F reaction vessel. The HF is evaporated under vaccum and the residue is washed with ether. The residue is dissolved in 10% acetic acid and lyophilized to yield 0.61 g of crude (pyro)-Glu-His-Trp-Ser-Tyr-3-(2-benzimidazolyl)-D-alanine-Leu-Arg-Pro-NH-$CH_2CH_3$ as its acetic acid addition salt. The crude peptide is partially purified by hydrophobic absorption chromatography on a non-functionalized polystyrenedivinylbenzene resin (Amberlyte XAD-4). The compound is eluted from the resin with a linear gradient (total 4 l) from 10% EtOH to 75% EtOH and fractions from 900 to 3200 ml are pooled.

The partially purified material thus obtained is finally purified by ion-exchange chromatography using Whatman carboxymethylcellulose (CM-52). The compound is eluted with a concave gradient (0.5–1.0 l) from 0.05 M NA4OAc (pH 7) to 0.15 M NH4OAc (pH 7). The major ultraviolet absorbing peak is pooled (Fraction 100–120) and lyophilixed three times to yield 0.12 g of pure pyro-glutamyl-histidyl-tryptophyl-seryl-tyrosyl-3-(2-benzimidazolyl)-D-alanyl-leucyl-arginyl-proline ethylamide as the acetic acid salt, $[\alpha]_D^{25} -27.7°$ (C 0.8, HOAc).

Repeating the above cleavage, substituting a stoichiometric amount of:
n-butylamine,
cyclopropylamine,
cyclohexylamine,
trifluoromethylamine,
pentafluoroethylamine, and
2,2,2-trifluoroethylamine
for ethylamine there are obtained the corresponding
n-butylamide,
cyclopropylamide,
cyclohexylamide,
trifluoromethylamide,
pentafluoroethylamide, and
2,2,2-trifluoroethylamide
of the aforementioned nonapeptide.

EXAMPLE 3

Compounds of Formula I wherein Z is

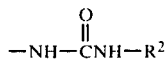

may be prepared by classical solution synthesis.

For example, the following approach may be used wherein "AzaGlyNH2"

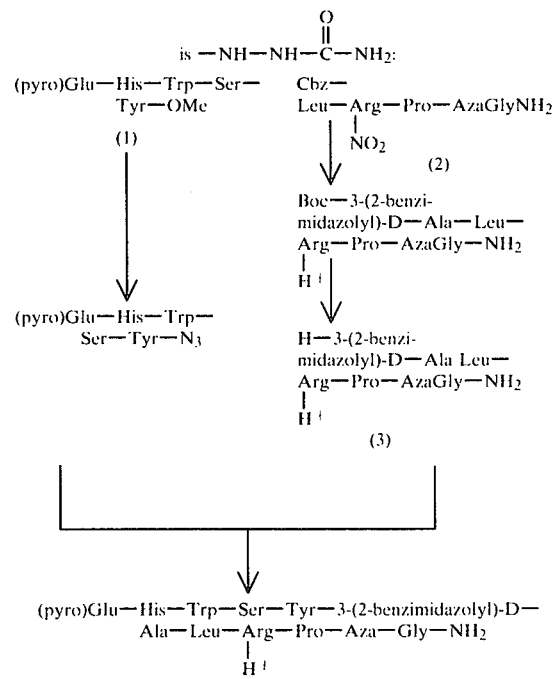

as the free peptide or salt.

The coupling of the individual fragments may proceed by the acyl azide method (J. Honzel, et al, *Coll. Czech. Chem. Comm*, 26, 2333 (1971)), by DCC/HBT coupling or other racemization free fragment coupling techniques. Compounds (1) and (2) are known (M. Fujino, et al, *Biochem. Biophys. Res. Comm.*, 57, 1248 (1974) and A. S. Dutta, et al., *J. Chem. Soc. Perkin I*, 1979, 379, respectively). Compound (3) is prepared from (2) by removal of the Cbz and nitro groups by hydrogenolysis, followed by coupling with $N^\alpha$-Boc-3-(2-benzimidazolyl)-D-alanine using DCC/HBT or other coupling agent known in the art. See Dutta, et al, supra, for a similar LH-RH analogue synthesis.

Similarly, utilizing other amino acids in place of $N^\alpha$-Boc-3-(2-benzimidazolyl)-D-alanine, other compounds of Formula I may be prepared, e.g.
(pyro)Glu-His-Trp-Ser-Tyr-3-(2-benzimidazolyl)-D-Ala-N-methyl-Leu-Arg-Pro-AzaGlyNH2 and
(pyro)Glu-His-Trp-Ser-Tyr-3-[2-(4,5,6,7-tetrahydrobenzimidazolyl)]-D-Ala-Leu-Arg-Pro-AzaGlyNH2. Also, in the preparation of compound (2), use of AzaGly-NH-lower alkyl in place of Aza-Gly-NH2 affords the corresponding peptide with an AzaGly-NH-lower alkyl terminus, e.g.
(pyro)Glu-His-Trp-Ser-Tyr-3-(2-benzimidazolyl)-D-Ala-Leu-Arg-Pro-AzaGly-NHEt,
(pyro)Glu-His-Trp-Ser-Tyr-3-(2-benzimidazolyl)-D-Ala-N-methyl-Leu-Arg-Pro-AzaGly-NHEt and
(pyro)Glu-His-Trp-Ser-Tyr-3-[2-(4,5,6,7-tetrahydrobenzimidazolyl)]-D-Ala-Leu-Arg-Pro-AzaGly-NHEt.

EXAMPLE 4

Repeating the procedure of Example 1 and utilizing either a D-amino acid or a D,L amino acid at position 6 (in the latter case, separating the diastereomeric peptides during chromatography), substituting the appropriate amino acids in the solid phase synthesis sequence, there may be obtained the following decapeptides which are isolated and characterized as their acetic acid addition salts:
pyro-glutamyl-histidyl-tryptophyl-seryl-tyrosyl-3-(2-benzimidazolyl)-D-alanyl-N-methylleucyl-arginyl-prolyl-glycinamide;
pyro-glutamyl-histidyl-phenylalanyl-seryl-tyrosyl-3-(2-benzimidazolyl)-D-alanyl-leucyl-arginyl-prolyl-glycinamide;
pyro-glutamyl-histidyl-3-(1-naphthyl)-L-alanyl-seryl-tyrosyl-3-(2-benzimidazolyl)-D-alanyl-leucyl-arginyl-prolyl-glycinamide;
pyro-glutamyl-histidyl-tryptophyl-seryl-phenylalanyl-3-(2-benzimidazolyl)-D-alanyl-leucyl-arginyl-prolyl-glycinamide;
pyro-glutamyl-histidyl-tryptophyl-seryl-3-(1-pentafluorophenyl)-L-alanyl-3-(2-benzimidazolyl)-D-alanyl-leucyl-arginyl-prolyl-glycinamide;
pyro-glutamyl-histidyl-tryptophyl-seryl-tyrosyl-3-[2-(5,6-dimethylbenzimidazolyl)]-D-alanyl-leucyl-arginyl-prolyl-glycinamide;
pyro-glutamyl-histidyl-tryptophyl-seryl-tyrosyl-3-[2-(5-chlorobenzimidazolyl)]-D-alanyl-leucyl-arginyl-prolyl-glycinamide;
pyro-glutamyl-histidyl-tryptophyl-seryl-tyrosyl-3-[2-(5,6-dichlorobenzimidazolyl)]-D-alanyl-leucyl-arginyl-prolyl-glycinamide;
pyro-glutamyl-histidyl-tryptophyl-seryl-tyrosyl-3-[2-(5-bromobenzimidazolyl)]-D-alanyl-leucyl-arginyl-prolyl-glycinamide;

pyro-glutamyl-histidyl-tryptophyl-seryl-tyrosyl-3-[2-(5-butylbenzimidazolyl)]-D-alanyl-leucyl-arginyl-prolyl-glycinamide;

pyro-glutamyl-histidyl-tryptophyl-seryl-tyrosyl-3-[2-(5-methylbenzimidazolyl)]-D-alanyl-leucyl-arginyl-prolyl-glycinamide;

pyro-glutamyl-histidyl-tryptophyl-seryl-tyrosyl-3-[2-(naphth[1,2-d]imidazolyl)]-D-alanyl-leucyl-arginyl-prolyl-glycinamide;

pyro-glutamyl-histidyl-tryptophyl-seryl-tyrosyl-3-[2-(7-methylnaphth[1,2-d]imidazolyl)]-D-alanyl-leucyl-arginyl-prolyl-glycinamide;

pyro-glutamyl-histidyl-tryptophyl-seryl-tyrosyl-3-[2-(naphth[2,3-d]imidazolyl)]-D-alanyl-leucyl-arginyl-prolyl-glycinamide;

pyro-glutamyl-histidyl-tryptophyl-seryl-tyrosyl-3-[2-(6-methylnaphth[2,3-d]imidazolyl)]-D-alanyl-leucyl-arginyl-prolyl-glycinamide;

pyro-glutamyl-histidyl-tryptophyl-seryl-tyrosyl-3-[2-(6,7-dimethylnaphth[2,3-d]imidazolyl)]-D-alanyl-leucyl-arginyl-prolyl-glycinamide;

pyro-glutamyl-histidyl-tryptophyl-seryl-tyrosyl-3-[2-(6-chloronaphth[2,3-d]imidazolyl)]-D-alanyl-leucyl-arginyl-prolyl-glycinamide;

pyro-glutamyl-histidyl-tryptophyl-seryl-tyrosyl-3-[2-(6-bromonaphth[2,3-d]imidazolyl)]-D-alanyl-leucyl-arginyl-prolyl-glycinamide;

pyro-glutamyl-histidyl-tryptophyl-seryl-tyrosyl-3-[2-(6-butylnaphth[2,3-d]imidazolyl)]-D-alanyl-leucyl-arginyl-prolyl-glycinamide;

pyro-glutamyl-histidyl-tryptophyl-seryl-tyrosyl-3-[2-(2-benzoxazolyl)]-D-alanyl-leucyl-arginyl-prolyl-glycinamide;

pyro-glutamyl-histidyl-tryptophyl-seryl-tyrosyl-3-[2-(5-methylbenzoxazolyl)]-D-alanyl-leucyl-arginyl-prolyl-glycinamide;

pyro-glutamyl-histidyl-tryptophyl-seryl-tyrosyl-3-[2-(5,6-dimethylbenzoxazolyl)]-D-alanyl-leucyl-arginyl-prolyl-glycinamide;

pyro-glutamyl-histidyl-tryptophyl-seryl-tyrosyl-3-[2-(5-chlorobenzoxazolyl)]-D-alanyl-leucyl-arginyl-prolyl-glycinamide;

pyro-glutamyl-histidyl-tryptophyl-seryl-tyrosyl-3-[2-(5-bromobenzoxazolyl)]-D-alanyl-leucyl-arginyl-prolyl-glycinamide;

pyro-glutamyl-histidyl-tryptophyl-seryl-tyrosyl-3-[2-(5-butylbenzoxazolyl)]-D-alanyl-leucyl-arginyl-prolyl-glycinamide;

pyro-glutamyl-histidyl-tryptophyl-seryl-tyrosyl-3-[2-(5,6-dichlorobenzoxazolyl)]-D-alanyl-leucyl-arginyl-prolyl-glycinamide;

pyro-glutamyl-histidyl-tryptophyl-seryl-tyrosyl-3-(2-benzothiazolyl)-D-alanyl-leucyl-arginyl-prolyl-glycinamide; m.p. 168°-178° (decomposition), $[\alpha]_D^{25} -35.5°$ (C 0.3, HOAc);

pyro-glutamyl-histidyl-tryptophyl-seryl-tyrosyl-3-[2-(5-methylbenzothiazolyl)]-D-alanyl-leucyl-arginyl-prolyl-glycinamide;

pyro-glutamyl-histidyl-tryptophyl-seryl-tyrosyl-3-[2-(5,6-dimethylbenzothiazolyl)]-D-alanyl-leucyl-arginyl-prolyl-glycinamide;

pyro-glutamyl-histidyl-tryptophyl-seryl-tyrosyl-3-[2-(5-chlorobenzothiazolyl)]-D-alanyl-leucyl-arginyl-prolyl-glycinamide;

pyro-glutamyl-histidyl-tryptophyl-seryl-tyrosyl-3-[2-(5-bromobenzothiazolyl)]-D-alanyl-leucyl-arginyl-prolyl-glycinamide;

pyro-glutamyl-histidyl-tryptophyl-seryl-tyrosyl-3-[2-(5,6-dichlorobenzothiazolyl)]-D-alanyl-leucyl-arginyl-prolyl-glycinamide;

pyro-glutamyl-histidyl-tryptophyl-seryl-tyrosyl-3-[2-(5-butylbenzothiazolyl)]-D-alanyl-leucyl-arginyl-prolyl-glycinamide;

pyro-glutamyl-histidyl-tryptophyl-seryl-tyrosyl-3-(2-naphth[2,1-d]oxazolyl)-D-alanyl-leucyl-arginyl-prolyl-glycinamide;

pyro-glutamyl-histidyl-tryptophyl-seryl-tyrosyl-3-(2-naphth[2,3-d]oxazolyl)-D-alanyl-leucyl-arginyl-prolyl-glycinamide;

pyro-glutamyl-histidyl-tryptophyl-seryl-tyrosyl-3-[2-(7-methylnaphth[2,1-d]oxazolyl)]-D-alanyl-leucyl-arginyl-prolyl-glycinamide;

pyro-glutamyl-histidyl-tryptophyl-seryl-tyrosyl-3-[2-(7,8-dimethylnaphth[2,1-d]oxazolyl)]-D-alanyl-leucyl-arginyl-prolyl-glycinamide;

pyro-glutamyl-histidyl-tryptophyl-seryl-tyrosyl-3-[2-(6-methylnaphth[2,3-d]oxazolyl)]-D-alanyl-leucyl-arginyl-prolyl-glycinamide;

pyro-glutamyl-histidyl-tryptophyl-seryl-tyrosyl-3-[2-(6,7-dimethylnaphth[2,3-d]oxazolyl)]-D-alanyl-leucyl-arginyl-prolyl-glycinamide;

pyro-glutamyl-histidyl-tryptophyl-seryl-tyrosyl-3-[2-(6-bromonaphth[2,3-d]oxazolyl)]-D-alanyl-leucyl-arginyl-prolyl-glycinamide;

pyro-glutamyl-histidyl-tryptophyl-seryl-tyrosyl-3-[2-(6-butylnaphth[2,3-d]oxazolyl)]-D-alanyl-leucyl-arginyl-prolyl-glycinamide;

pyro-glutamyl-histidyl-tryptophyl-seryl-tyrosyl-3-[2-(6-chloronaphth[2,3-d]oxazolyl)]-D-alanyl-leucyl-arginyl-prolyl-glycinamide;

pyro-glutamyl-histidyl-tryptophyl-seryl-tyrosyl-3-[2-(6,7-dichloronaphth[2,3-d]oxazolyl)]-D-alanyl-leucyl-arginyl-prolyl-glycinamide;

pyro-glutamyl-histidyl-tryptophyl-seryl-tyrosyl-3-[2-(4,5,6,7-tetrahydrobenzimidazolyl)]-D-alanyl-leucyl-arginyl-prolyl-glycinamide;

pyro-glutamyl-histidyl-tryptophyl-seryl-tyrosyl-3-[2-(4,5,6,7-tetrahydrobenzimidazolyl)]-D-alanyl-N-methylleucyl-arginyl-prolyl-glycinamide, m.p. 162°-170° C. (with decomposition);

pyro-glutamyl-histidyl-tryptophyl-seryl-tyrosyl-3-[2-(5-methyl-4,5,6,7-tetrahydrobenzimidazolyl)]-D-alanyl-leucyl-arginyl-prolyl-glycinamide;

pyro-glutamyl-histidyl-tryptophyl-seryl-tyrosyl-3-[2-(5,6-dimethyl-4,5,6,7-tetrahydrobenzimidazolyl)]-D-alanyl-leucyl-arginyl-prolyl-glycinamide;

pyro-glutamyl-histidyl-tryptophyl-seryl-tyrosyl-3-[2-(5-chloro-4,5,6,7-tetrahydrobenzimidazolyl)]-D-alanyl-leucyl-arginyl-prolyl-glycinamide;

pyro-glutamyl-histidyl-tryptophyl-seryl-tyrosyl-3-[2-(5,6-dichloro-4,5,6,7-tetrahydrobenzimidazolyl)]-D-alanyl-leucyl-arginyl-prolyl-glycinamide;

pyro-glutamyl-histidyl-tryptophyl-seryl-tyrosyl-3-[2-(5-bromo-4,5,6,7-tetrahydrobenzimidazolyl)]-D-alanyl-leucyl-arginyl-prolyl-glycinamide;

pyro-glutamyl-histidyl-tryptophyl-seryl-tyrosyl-3-[2-(5-butyl-4,5,6,7-tetrahydrobenzimidazolyl)]-D-alanyl-leucyl-arginyl-prolyl-glycinamide;

pyro-glutamyl-histidyl-tryptophyl-seryl-tyrosyl-3-[2-(4,5,6,7-tetrahydrobenzothiazdyl)]-D-alanyl-leucyl-arginyl-prolyl-glycinamide;

pyro-glutamyl-histidyl-tryptophyl-seryl-tyrosyl-3-[2-(5-methyl-4,5,6,7-tetrahydrobenzothiazolyl)]-D-alanyl-leucyl-arginyl-prolyl-glycinamide;

pyro-glutamyl-histidyl-tryptophyl-seryl-tyrosyl-3-[2-(5,6-dimethyl-4,5,6,7-tetrahydrobenzothiazolyl)]-D-alanyl-leucyl-arginyl-prolyl-glycinamide;

pyro-glutamyl-histidyl-tryptophyl-seryl-tyrosyl-3-[2-(5-chloro-4,5,6,7-tetrahydrobenzothiazolyl)]-D-alanyl-leucyl-arginyl-prolyl-glycinamide;

pyro-glutamyl-histidyl-tryptophyl-seryl-tyrosyl-3-[2-(5,6-dichloro-4,5,6,7-tetrahydrobenzothiazolyl)]-D-alanyl-leucyl-arginyl-prolyl-glycinamide;

pyro-glutamyl-histidyl-tryptophyl-seryl-tyrosyl-3-[2-(4,5,6,7-tetrahydrobenzoxazolyl)]-D-alanyl-leucyl-arginyl-prolyl-glycinamide;

pyro-glutamyl-histidyl-tryptophyl-seryl-tyrosyl-3-[2-(5-methyl-4,5,6,7-tetrahydrobenzoxazolyl)]-D-alanyl-leucyl-arginyl-prolyl-glycinamide;

pyro-glutamyl-histidyl-tryptophyl-seryl-tyrosyl-3-[2-(5,6-dimethyl-4,5,6,7-tetrahydrobenzoxazolyl)]-D-alanyl-leucyl-arginyl-prolyl-glycinamide;

pyro-glutamyl-histidyl-tryptophyl-seryl-tyrosyl-3-[2-(5-chloro-4,5,6,7-tetrahydrobenzoxazolyl)]-D-alanyl-leucyl-arginyl-prolyl-glycinamide;

pyro-glutamyl-histidyl-tryptophyl-seryl-tyrosyl-3-[2-(5,6-dichloro-4,5,6,7-tetrahydrobenzoxazolyl)]-D-alanyl-leucyl-arginyl-prolyl-glycinamide;

pyro-glutamyl-histidyl-tryptophyl-seryl-tyrosyl-3-[2-(4,5,5a,6,7,8,9,9a-octohydronaphth[1,2-d]imidazolyl)]-D-alanyl-leucyl-arginyl-prolyl-glycinamide;

pyro-glutamyl-histidyl-tryptophyl-seryl-tyrosyl-3-[2-(4,4a,5,6,7,8,8a,9-octohydronaphth[1,2-d]imidazolyl)]-D-alanyl-leucyl-arginyl-prolyl-glycinamide;

pyro-glutamyl-histidyl-tryptophyl-seryl-tyrosyl-3-[2-(6-methyl-4,4a,5,6,7,8,8a,9-octohydronaphth[2,3-d]imidazolyl)]-D-alanyl-leucyl-arginyl-prolyl-glycinamide;

pyro-glutamyl-histidyl-tryptophyl-seryl-tyrosyl-3-[2-(6-chloro-4,4a,5,6,7,8,8a,9-octohydronaphth[2,3-d]imidazolyl)]-D-alanyl-leucyl-arginyl-prolyl-glycinamide;

pyro-glutamyl-histidyl-tryptophyl-seryl-tyrosyl-3-[2-(6,7-dimethyl-4,4a,5,6,7,8,8a,9-octohydronaphth[2,3-d]-imidazolyl)]-D-alanyl-leucyl-arginyl-prolyl-glycinamide;

pyro-glutamyl-histidyl-tryptophyl-seryl-tyrosyl-3-[2-(6,7-dichloro-4,4a,5,6,7,8,8a,9-octohydronaphth[2,3-d]imidazolyl)]-D-alanyl-leucyl-arginyl-prolyl-glycinamide;

pyro-glutamyl-histidyl-tryptophyl-seryl-tyrosyl-3-[2-(6-bromo-4,4a,5,6,7,8,8a,9-octohydronaphth[2,3-d]-imidazolyl)]-D-alanyl-leucyl-arginyl-prolyl-glycinamide;

pyro-glutamyl-histidyl-tryptophyl-seryl-tyrosyl-3-[2-(6-butyl-4,4a,5,6,7,8,8a,9-octohydronaphth[2,3-d]-imidazolyl)]-D-alanyl-leucyl-arginyl-prolyl-glycinamide;

pyro-glutamyl-histidyl-tryptophyl-seryl-tyrosyl-3-[2-(4,4a,5,6,7,8,8a,9-octohydronaphtho[2,3-d]thiazolyl)]-D-alanyl-leucyl-arginyl-prolyl-glycinamide;

pyro-glutamyl-histidyl-tryptophyl-seryl-tyrosyl-3-[2-(6-methyl-4,4a,5,6,7,8,8a,9-octohydronaphtho[2,3-d]thiazolyl)]-D-alanyl-leucyl-arginyl-prolyl-glycinamide;

pyro-glutamyl-histidyl-tryptophyl-seryl-tyrosyl-3-[2-(6-chloro-4,4a,5,6,7,8,8a,9-octohydronaphtho[2,3-d]thiazolyl)]-D-alanyl-leucyl-arginyl-prolyl-glycinamide;

pyro-glutamyl-histidyl-tryptophyl-seryl-tyrosyl-3-[2-(4,5,5a,6,7,8,9,9a-octohydronaphth[2,1-d]oxazolyl)]-D-alanyl-leucyl-arginyl-prolyl-glycinamide;

pyro-glutamyl-histidyl-tryptophyl-seryl-tyrosyl-3-[2-(4,4a,5,6,7,8,8a,9-octohydronaphth[2,3-d]oxazolyl)]-D-alanyl-leucyl-arginyl-prolyl-glycinamide;

pyro-glutamyl-histidyl-tryptophyl-seryl-tyrosyl-3-[2-(6-methyl-4,4a,5,6,7,8,8a,9-octohydronaphth[2,3-d]oxazolyl)]-D-alanyl-leucyl-arginyl-prolyl-glycinamide;

pyro-glutamyl-histidyl-tryptophyl-seryl-tyrosyl-3-[2-(6-chloro-4,4a,5,6,7,8,8a,9-octohydronaphth[2,3-d]oxazolyl)]-D-alanyl-leucyl-arginyl-prolyl-glycinamide.

EXAMPLE 5

Repeating the procedure of Example 2 and utilizing either a D-amino acid or a D,L amino acid at position 6 (in the latter case, separating the diastereomeric peptides during chromatography), substituting the appropriate amino acids in the solid phase synthesis sequence, there may be obtained the following nonapeptides which are isolated and characterized as their acetic acid addition salts:

pyro-glutamyl-histidyl-tryptophyl-seryl-tyrosyl-3-(2-benzimidazolyl)-D-alanyl-leucyl-arginyl-proline as its ethylamide, (as the acetic acid salt, $[\alpha]_D^{25} -27.7°$ (C 0.8, HOAc), n-butylamide, cyclopropylamide, cyclohexylamide, trifluoromethylamide, pentafluoroethylamide and 2,2,2-trifluoroethylamide;

pyro-glutamyl-histidyl-phenylalanyl-seryl-tyrosyl-3-(2-benzimidazolyl)-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-3-(1-naphthyl)-L-alanyl-seryl-tyrosyl-3-(2-benzimidazolyl)-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-phenylalanyl-3-(2-benzimidazolyl)-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-3-(1-pentafluorophenyl)-L-alanyl-3-(2-benzimidazolyl)-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(5-methylbenzimidazolyl)]-D-alanyl-leucyl-arginyl-proline as its ethylamide, n-butylamide, cyclopropylamide, cyclohexylamide, trifluoromethylamide, pentafluoro-ethylamide and 2,2,2-trifluoroethylamide;

pyro-glutamyl-histidyl-tryptophyl-seryl-tyrosyl-3-[2-(5,6-dimethylbenzimidazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(5-chlorobenzimidazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(5,6-dichlorobenzimidazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(5-bromobenzimidazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(5-butylbenzimidazolyl)]-D-alanyl-leucyl-arginyl-proline as its ethylamide, n-butylamide, cyclopropyl amide, cyclohexylamide, trifluoromethylamide, pentafluoroethylamide and 2,2,2-trifluoroethylamide;

pyro-glutamyl-histidyl-tryptophyl-seryl-tyrosyl-3-(2-benzoxazolyl)-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(6-methylbenzoxazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(5,6-dimethylbenzoxazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(6-chlorobenzoxazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(5,6-dichlorobenzoxazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(5-bromobenzoxazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(5-butylbenzoxazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-(2-benzothiazolyl)-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(6-methylbenzothiazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(5,6-dimethylbenzothiazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(6-chlorobenzothiazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(5,6-dichlorobenzothiazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(5-bromobenzothiazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(5-butylbenzothiazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-(2-naphth[2,1-d]oxazolyl)-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-(2-naphth[2,3-d]oxazolyl)-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(7-methylnaphth[2,1-d]oxazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(7,8-dimethylnaphth[2,1-d]oxazolyl]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(6-methylnaphth[2,3-d]oxazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(6,7-dimethylnaphth[2,3-d]oxazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-2-(6-chloronaphth[2,3-d]oxazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(6,7-dichloronaphth[2,3-d]oxazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(4,5,6,7-tetrahydrobenzimidazolyl)]-D-alanyl-leucyl-arginyl-proline as its ethylamide, m.p. 175°–188°, $[\alpha]_D^{25}$ −29.7° (C 0.4, HOAc), n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(5-methyl-4,5,6,7-tetrahydrobenzimidazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(5,6-dimethyl-4,5,6,7-tetrahydrobenzimidazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(5-chloro-4,5,6,7-tetrahydrobenzimidazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(5,6-dichloro-4,5,6,7-tetrahydrobenzimidazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(4,5,6,7-tetrahydrobenzothiazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(5-methyl-4,5,6,7-tetrahydrobenzothiazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(5,6-dimethyl-4,5,6,7-tetrahydrobenzothiazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(5-chloro-4,5,6,7-tetrahydrobenzothiazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(5,6-dichloro-4,5,6,7-tetrahydrobenzothiazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(4,5,6,7-tetrahydrobenzoxazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(5-methyl-4,5,6,7-tetrahydrobenzoxazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(5,6-dimethyl-4,5,6,7-tetrahydrobenzoxazolyl)]-D-alanyl-leucyl-arginyl-proline as its ethylamide, n-butylamide, cyclopropylamide, cyclohexylamide, trifluoromethylamide; pentafluoroethylamide and 2,2,2-trifluoroethylamide;

pyro-glutamyl-histidyl-tryptophyl-seryl-tyrosyl-3-[2-(5-chloro-4,5,6,7-tetrahydrobenzoxazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(5,6-dichloro-4,5,6,7-tetrahydrobenzoxazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(4,5,5a,6,7,8,9,9a-octohydronaphth[1,2-d]imidazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(4,4a,5,6,7,8,8a,9-octohydronaphth[2,3-d]imidazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(6-methyl-4,4a,5,6,7,8,8a,9-octohydronaphth[2,3-d]imidazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(6-chloro-4,4a,5,6,7,8,8a,9-octohydronaphth[2,3-d]imidazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(4,4a,5,6,7,8,8a,9-octohydronaphtho[2,3-d]thiazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(6-methyl-4,4a,5,6,7,8,8a,9-octohydronaphtho[2,3-d]thiazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(6-chloro-4,4a,5,6,7,8,8a,9-octohydronaphtho[2,3-d]thiazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(4,4a,5,6,7,8,8a,9-octohydronaphth[2,3-d]oxazolyl)]-

D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(6-methyl-4,4a,5,6,7,8,8a,9-octohydronaphth[2,3-d]-oxazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(6-chloro-4,4a,5,6,7,8,8a,9-octohydronaphth[2,3-d]-oxazolyl)]-D-alanyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-(2-benzimidazolyl)-D-alanyl-N-methylleucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-(2-benzimidazolyl)-D-alanyl-isoleucyl-arginyl-proline as its ethylamide, n-butylamide, cyclopropylamide, cyclohexylamide, trifluoromethylamide, pentafluoroethylamide and 2,2,2-trifluoroethylamide, and pyro-glutamyl-histidyl-tryptophyl-seryl-tyrosyl-3-(2-benzimidazolyl)-D-alanyl-norleucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(naphth[2,3-d]imidazolyl)]-D-alanyl-N-methylleucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(naphth[2,3-d]imidazolyl)]-D-alanyl-isoleucyl-arginyl-proline as its ethylamide, m.p. 177°–187°, $[\alpha]_D^{25} -27.5°$ (C 0.3, HOAc), n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(naphth[2,3-d]imidazolyl)]-D-alanyl-norleucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(4,5,6,7-tetrahydrobenzimidazolyl)]-D-alanyl-N-methylleucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(4,5,6,7-tetrahydrobenzimidazolyl)]-D-alanyl-isoleucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(4,5,6,7-tetrahydrobenzimidazolyl)]-D-alanyl-norleucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-(2-benzothiazolyl)-D-alanyl-N-methylleucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-(2-benzothiazolyl)-D-alanyl-N-isoleucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-(2-benzothiazolyl)-D-alanyl-N-norleucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-(2-benzoxazolyl)-D-alanyl-N-methylleucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-(2-benzoxazolyl)-D-alanyl-isoleucyl-arginyl-proline as its ethylamide, n-butylamide, cyclopropylamide, cyclohexylamide, trifluoromethylamide, pentafluoroethylamide and 2,2,2-trifluoroethylamide, and pyro-glutamyl-histidyl-tryptophyl-seryl-tyrosyl-3-(2-benzoxazolyl)-D-alanyl-norleucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(4,5,6,7-tetrahydrobenzothiazolyl)]-D-alanyl-N-methyl-leucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(4,5,6,7-tetrahydrobenzothiazolyl)]-D-alanyl-isoleucyl-arginyl-proline as its ethylamide, n-butylamide, cyclopropylamide, cyclohexylamide, trifluoromethylamide, pentafluoroethylamide and 2,2,2-trifluoroethylamide, pyro-glutamyl-histidyl-tryptophyl-seryl-tyrosyl-3-[2-(4,5,6,7-tetrahydrobenzothiazolyl)]-D-alanyl-norleucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(4,5,6,7-tetrahydrobenzoxazolyl)]-D-alanyl-N-methylleucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(4,5,6,7-tetrahydrobenzoxazolyl)]-D-alanyl-isoleucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(4,5,6,7-tetrahydrobenzoxazolyl)]-D-alanyl-norleucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(4,4a,5,6,7,8,8a,9-octahydronaphth[2,3-d]imidazolyl)]-D-alanyl-N-methylleucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(4,4a,5,6,7,8,8a,9-octahydronaphth[2,3-d]imidazolyl)]-D-alanyl-isoleucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(4,4a,5,6,7,8,8a,9-octahydronaphth[2,3-d]imidazolyl)]-D-alanyl-norleucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(4,4a,5,6,7,8,8a,9-octahydronaphtho[2,3-d]thiazolyl)]-D-alanyl-N-methylleucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(4,4a,5,6,7,8,8a,9-octahydronaphtho[2,3-d]thiazolyl)]-D-alanyl-isoleucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(4,4a,5,6,7,8,8a,9-octahydronaphtho[2,3-d]thiazolyl)]-D-alanyl-norleucyl-arginyl-proline as its ethylamide, n-butylamide, cyclopropylamide, cyclohexylamide, trifluoromethylamide, pentafluoroethylamide and 2,2,2-trifluoroethylamide;

pyro-glutamyl-histidyl-tryptophyl-seryl-tyrosyl-3-[2-(4,4a,5,6,7,8,8a,9-octohydronaphth[2,3-d]oxazolyl)]-D-alanyl-N-methylleucyl-arginyl-proline as its ethylamide, n-butylamide, cyclopropylamide, cyclohexylamide, trifluoroethylamide, pentafluoroethylamide and 2,2,2-trifluoroethylamide;

pyro-glutamyl-histidyl-tryptophyl-seryl-tyrosyl-3-[2-(4,4a,5,6,7,8,8a,9-octohydronaphth[2,3-d]oxazolyl)]-D-alanyl-isoleucyl-arginyl-proline as its ethylamide, n-butylamide, cyclopropylamide, cyclohexylamide, trifluoromethylamide, pentafluoroethylamide and 2,2,2-trifluoroethylamide, and pyro-glutamyl-histidyl-tryptophyl-seryl-tyrosyl-3-[2-(4,4a,5,6,7,8,8a,9-octohydronaphth[2,3-d]oxazolyl)]-D-alanyl-norleucyl-arginyl-proline as its ethylamide, n-butylamide, cyclopropylamide, cyclohexylamide, trifluoromethylamide, pentafluoroethylamide and 2,2,2-trifluoroethylamide.

EXAMPLE 6

A. A solution of 0.1 g of the hydrogen fluoride salt of (pyro)Glu-His-Trp-Ser-Tyr-3-(2-benzimidazolyl)-D-Ala-Leu-Arg-Pro-Gly-NH$_2$ (See Example 1) is dissolved in 50 ml of water and passed through a column of 50 g Dowex 3 anion exchange resin which had previously been equilibrated with acetic acid and washed with deionized water. The column is eluted with deionized water and the effluent is lyophilized to yield the corresponding acetic acid (pyro)Glu-His-Trp-Ser-Tyr-3-(2-benzimidazolyl)-D-Ala-Leu-Arg-Pro-Gly-NH$_2$, m.p. 175°–182° C. (with decomposition) $[\alpha]_D^{25} -27.7°$ (C 0.9, HOAc).

Repeating the above, substituting other acids for acetic acid during the equilibration of the resin, there may be obtained, for example, the corresponding salts with hydrochloric acid, hydrobromic acid, sulfuric acid, phosphoric acid, nitric acid, benzoic acid, and the like.

Similarly there may be prepared the acid addition salts of other compounds of Formula I.

B. In the case of salts of low water solubility, these may be prepared by precipitation from water utilizing the desired acid. For example:

Zinc tannate salt—a solution of 10 mg of (pyro)Glu-His-Trp-Ser-Tyr-3-(2-benzimidazolyl)-D-Ala-Leu-Arg-Pro-Gly-NH$_2$ acetic acid salt in 0.1 ml of water is treated with a solution of 8 mg of tannic acid in 0.08 ml of 0.25 M NaOH. A solution of 5 mg of ZnSO$_4$ heptahydrate in 0.1 ml of water is immediately added to the solution of the LH-RH analogue.

The resultant suspension is diluted with 1 ml water and the precipitate is centrifuged. The supernatant is decanted and the residue is washed twice with 1 ml portions of water by centrifugation of the precipitate and decantation of the supernatant. The precipitate is dried in vacuo to yield 15 mg of the mixed zinc tannate salt of the above named LH-RH analogue.

Pamoate salt—to a solution of 50 mg (pyro)Glu-His-Trp-Ser-Tyr-3-(2-benzimidazolyl)-D-Ala-Leu-Arg-Pro-Gly-NH$_2$ acetic acid salt in a mixture of 1.6 ml of ethanol and 0.1 ml of 0.25 M NaOH is added solution of 11 mg of pamoic acid in 0.3 ml of 0.25 M NaOH. The solvents are removed at reduced pressure and the residue is suspended in 2 ml of water, centrifuged, and the supernatant is decanted. The precipitate is washed with 1.5 ml H$_2$O, centrifuged, and the supernatant is decanted. The precipitate is dried in vacuo to yield 54 mg of the pamoate salt of the above named LH-RH analogue.

In a similar manner other salts of low water solubility may be prepared.

C. Preparation of acid addition salt from free peptide.

To a solution of 50 mg of (pyro)Glu-His-Trp-Ser-Tyr-3-(2-benzimidazolyl)-D-Ala-Leu-Arg-Pro-Gly-NH$_2$ as the free base is added 30 ml of 1 N acetic acid. The resulting solution is lyophilized to yield 50 mg of the acetic acid salt of the above-named LH-RH analogue.

Similarly, replacing acetic acid with other acids (in stoichiometrically equivalent amounts relative to peptide) there is obtained other acid addition salts of compounds of Formula (I), for example, the salts with hydrochloric acid, hydrobromic acid, sulfuric acid, phosphoric acid, nitric acid.

D. Preparation of salt with metal cation, e.g., zinc salt.

To a solution of 50 mg (pyro)Glu-His-Trp-Ser-Tyr-3-(2-benzimidazolyl)-D-Ala-Leu-Arg-Pro-Gly-NH$_2$ acetic acid salt in a mixture of 0.4 ml of 0.25 M NaOH, 0.3 ml water, and 1 ml ethanol is added a solution of 15 mg of ZnSO$_4$ heptahydrate in 0.2 ml of water. The precipitate is centrifuged and the supernatant is decanted. The precipitate is washed with 1 ml of water by centrifugation and decantation of the supernatant. The precipitate is dried in vacuo to yield 48 mg of the zinc salt of the above named LH-RH analogue.

In a similar manner salts with other multivalent cations e.g. calcium, bismuth, barium, magnesium, aluminum, copper, cobalt, nickel, cadmium and the like, may be prepared.

EXAMPLE 7

A solution of 50 mg of (pyro)Glu-His-Trp-Ser-Tyr-3-(2-benzimidazolyl)-D-Ala-Leu-Arg-Pro-Gly-$NH_2$ acetic acid salt in 25 ml of water is passed through a 50 g column of Dowex 1 (strongly basic, quaternary ammonium anion exchange resin) which had been equilibrated with NaOH solution to make the counter ion hydroxide. The column is eluted with 150 ml of water and the eluant is lyophilized to yield 45 mg of the corresponding polypeptide as the free base.

Similarly other acid additions salts of compounds of Formula (I), e.g. those mentioned in Example 6, may be converted to the corresponding free bases.

EXAMPLE 8

The following are typical pharmaceutical compositions containing, as active ingredient, an LH-RH analogue of the present invention, for example (pyro)Glu-His-Trp-Ser-Tyr-3-(2-benzimidazolyl)-D-alanyl-Leu-Arg-Pro-Gly-$NH_2$, by itself or as a pharmaceutically acceptable salt, e.g. the acetic acid addition salt, the zinc salt, the zinc tannate salt, etc.

A. Tablet formulations for buccal (e.g. sublingual) administration:

| 1. | LH-RH Analogue | 50.0 μg |
|---|---|---|
|  | Compressible Sugar, USP | 96.0 mg |
|  | Calcium Stearate | 4.0 mg |
| 2. | LH-RH Analogue | 30.0 μg |
|  | Compressible Sugar, USP | 98.5 mg |
|  | Magnesium Stearate | 1.5 mg |
| 3. | LH-RH Analogue | 25.0 μg |
|  | Mannitol, USP | 88.5 mg |
|  | Magnesium Stearate, USP | 1.5 mg |
|  | Pregelatinized Starch, USP | 10.0 mg |
| 4. | LH-RH Analogue | 200.0 μg |
|  | Lactose, USP | 83.3 mg |
|  | Pregelatinized Starch, USP | 15.0 mg |
|  | Magnesium Stearate, USP | 1.5 mg |

Method of Manufacture a. LH-RH Analogue is dissolved in water, a sufficient quantity to form a wet granulation when mixed with the sugar portion of the excipients. After complete mixing, the granulation is dried in a tray or fluid-bed dryer. The dry granulation is then screened to break up any large aggregates and then mixed with the remaining components. The granulation is then compressed on a standard tabletting machine to the specific tablet weight.

b. In this manufacturing method, all formulations would include 0.01% gelatin, USP. The gelatin would be first dissolved in the aqueous granulation solvent followed by the LH-RH analog. The remaining steps are as in (a) above.

Formulation 4 could also be used as a tablet for oral administration.

B. Long Acting intramuscular injectable formulation.

| 1. Long Acting I.M. Injectable - Sesame Oil Gel | |
|---|---|
| LH-RH Analogue | 1.0 mg |
| Aluminum monostearate, USP | 20.0 mg |
| Sesame oil q.s. ad | 1.0 ml |

The aluminum monostearate is combined with the sesame oil and heated to 125° C. with stirring until a clear yellow solution forms. This mixture is then autoclaved for sterility and allowed to cool. The LH-RH analogue is then added aseptically with trituration. Particularly preferred LH-RH analogues are salts of low solubility, e.g. zinc salts, zinc tannate salts, pamoate salts, and the like. These exhibit exceptionally long duration of activity.

| 2. Long Acting I.M. Injectable - Biodegradable Polymer Microcapsules | |
|---|---|
| LH-RH Analogue | 1% |
| 25/75 glycolide/lactide copolymer (0.5 intrinsic viscosity) | 99% |

Microcapsules (0-150μ) of above formulation suspended in:

| | |
|---|---|
| Dextrose | 5.0% |
| CMC, sodium | 0.5% |
| Benzyl alcohol | 0.9% |
| Tween 80 | 0.1% |
| Water, purified q.s. | 100.0% |

25 mg of microcapsules would be suspended in 1.0 ml of vehicle.

| C. Aqueous Solution for Intramuscular Injection | |
|---|---|
| LH-RH Analogue | 25 mg |
| Gelatin, nonantigenic | 5 mg |
| Water for injection q.s. ad | 100 ml |

Dissolve gelatin and LH-RH analogue in water for injection, then sterile filter solution.

| D. Aqueous Solution for Nasal Administration | |
|---|---|
| LH-RH Analogue | 250 mg |
| Dextrose | 5 gm |
| Benzyl alcohol | 0.9 gm |
| Water, purified q.s. ad | 100 ml |

Dissolve LH-RH analogue, dextrose, benzyl alcohol in purified water and q.s. to volume.

| Suppository Vehicle for Rectal Administration | |
|---|---|
| LH-RH Analogue | 500 μg |
| Witepsol H15 | 20.0 gm |

The LH-RH analogue is combined with the molten Witepsol H15, mixed well and poured into 2 gm molds.

What is claimed is:

1. A compound of the formula $$(pyro)Glu-His-V-Ser-W-X-Y-Arg-Pro-Z \quad (I)$$

and the pharmaceutically acceptable salts thereof wherein:

V is tryptophyl, phenylalanyl or 3-(1-naphthyl)-L-alanyl;

W is tyrosyl, phenylalanyl or 3-(1-pentafluorophenyl)-L-alanyl;

X is a D-amino acid residue of the formula:

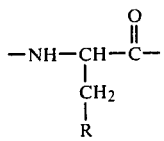

wherein R is a heterocyclic aryl radical selected from the group consisting of radicals represented by the following structural formulas:

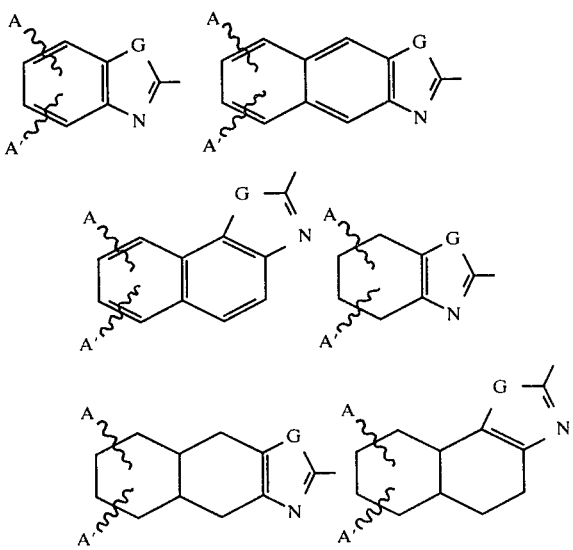

wherein A and A' are independently selected from the group consisting of hydrogen, lower alkyl, chlorine, and bromine, and G is selected from the group consisting of oxygen, nitrogen, and sulfur; Y is leucyl, isoleucyl, nor-leucyl or N-methyl-leucyl; Z is glycinamide or —NH—R$^1$, wherein R$^1$ is lower alkyl, cycloalkyl, fluoro lower alkyl or

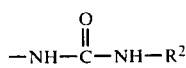

wherein:
R$^2$ is hydrogen or lower alkyl.

2. The compound of claim 1 wherein V is tryptophyl or phenylalanyl; W is tyrosyl; X is 3-(2-benzimidazolyl)-D-alanyl; 3-(2-naphth[1,2-d]-imidazolyl)-D-alanyl; 3-[2-(4,5,6,7-tetrahydrobenzimidazolyl)]-D-alanyl; 3-[2-(naphth[2,3-d]imidazolyl)]-D-alanyl; or 3-(2-benzothiazolyl)-D-alanyl; Y is leucyl or N-methylleucyl; and Z is glycinamide or prolylethylamide.

3. The compound of claim 2 wherein X is 3-(2-benzimidazolyl)-D-alanyl.

4. The compound of claim 2 wherein said compound is (pyro)Glu-His-Trp-Ser-Tyr-3-(2-benzimidazolyl)-D-alanyl-Leu-Arg-Pro-Gly-NH$_2$ or the pharmaceutically acceptable salt thereof.

5. The compound of claim 3 wherein said compound is (pyro)Glu-His-Trp-Ser-Tyr-3-(2-benzimidazolyl)-D-alanyl-N-methyl-Leu-Arg-Pro-Gly-NH$_2$ or a pharmaceutically acceptable salt thereof.

6. The compound of claim 3 wherein said compound is (pyro)Glu-His-Trp-Ser-Tyr-3-(2-benzimidazolyl)-D-alanyl-Leu-Arg-Pro-NHEt or a pharmaceutically acceptable salt thereof.

7. The compound of claim 3 wherein said compound is (pyro)Glu-His-Trp-Ser-Tyr-3-(2-benzimidazolyl)-D-alanyl-N-methyl-Leu-Arg-Pro-NHEt or a pharmaceutically acceptable salt thereof.

8. The compound of claim 3 wherein said compound is (pyro)Glu-His-Phe-Ser-Tyr-3-(2-benzimidazolyl)-D-alanyl-Leu-Arg-Pro-Gly-NH$_2$ or a pharmaceutically acceptable salt thereof.

9. The compound of claim 2 wherein X is 3-(2-naphth[2,3-d]imidazolyl)-D-alanyl.

10. The compound of claim 9 wherein said compound is (pyro)Glu-His-Trp-Ser-Tyr-3-[2-naphth[2,3-d]-imidazolyl]-D-alanyl-Leu-Arg-Pro-Gly-NH$_2$ or a pharmaceutically acceptable salt thereof.

11. The compound of claim 2 wherein X is 3-[2-(4,5,6,7-tetrahydrobenzimidazolyl)]-D-alanyl.

12. The compound of claim 11 wherein said compound is (pyro)Glu-His-Trp-Ser-Tyr-3-[2-(4,5,6,7-tetrahydrobenzimidazolyl)]-D-alanyl-Leu-Arg-Pro-Gly-NH$_2$ or a pharmaceutically acceptable salt thereof.

13. The compound of claim 2 wherein said compound is (pyro)Glu-His-Trp-Ser-Tyr-3-[2-(4,5,6,7-tetrahydrobenzimidazolyl)]-D-alanyl-Leu-Arg-Pro-NHEt or a pharmaceutically acceptable salt thereof.

14. The compound of claim 2 wherein X is 3-[2-(4,4a,5,6,7,8,8a,9-tetrahydronaphth[2,3-d]imidazolyl)]-D-alanyl.

15. The compound of claim 14 wherein said compound is (pyro)Glu-His-Trp-Ser-Tyr-3-[2-(4,4a,5,6,7,8,8a,9-tetrahydronaphth[2,3-d]imidazolyl)]-D-alanyl-Leu-Arg-Gly-NH$_2$ or a pharmaceutically acceptable salt thereof.

16. The compound of claim 2 wherein X is 3-(2-benzothiazolyl)-D-alanyl.

17. The compound of claim 16 wherein said compound is (pyro)Glu-His-Trp-Ser-Tyr-3-(2-benzothiazolyl)-D-alanyl-Leu-Arg-Pro-Gly-NH$_2$ or a pharmaceutically acceptable salt thereof.

18. A method of inhibiting ovulation in a female mammalian subject which method comprises administering to said subject an effective amount of a compound of the formula:

(pyro)Glu—His—V—Ser—W—X—Y—Arg—Pro—Z   (I)

or a pharmaceutically acceptable salt thereof wherein:
V is tryptophyl, phenylalanyl or 3-(1-naphthyl)-L-alanyl;
W is tyrosyl, phenylalanyl or 3-(1-pentafluorophenyl)-L-alanyl;
X is a D-amino acid residue of the formula:

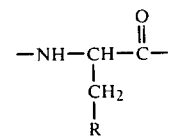

wherein R is a heterocyclic aryl radical selected from the group consisting of radicals represented by the following structural formulas:

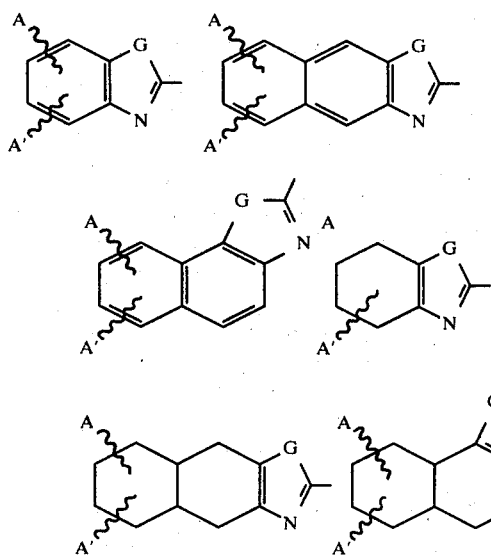

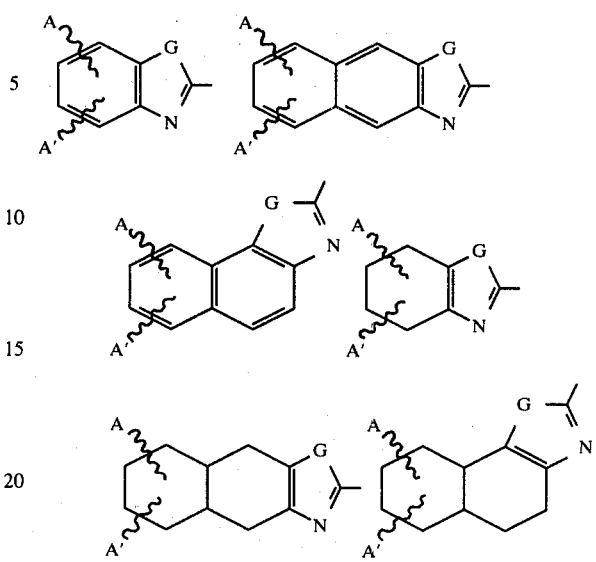

wherein A and A' are independently selected from the group consisting of hydrogen, lower alkyl, chlorine, and bromine, and G is selected from the group consisting of oxygen, nitrogen, and sulfur;

Y is leucyl, isoleucyl, nor-leucyl or N-methyl-leucyl;

Z is glycinamide or —NH—R¹, wherein

R¹ is lower alkyl, cycloalkyl, fluoro lower alkyl or

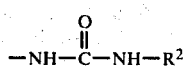

wherein:

R² is hydrogen or lower alkyl;

or a pharmaceutical composition containing same.

19. A method of treating endometriosis in a female mammalian subject which method comprises administering to said subject an effective amount of a compound of the formula (pyro)Glu—His—V—Ser—W—X—Y—Arg—Pro—Z  (I)

or a pharmaceutically acceptable salt thereof wherein:

V is tryptophyl, phenylalanyl or 3-(1-naphthyl)-L-alanyl;

W is tyrosyl, phenylalanyl or 3-(1-pentafluorophenyl)-L-alanyl;

X is a D-amino acid residue of the formula:

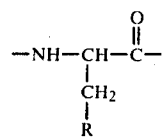

wherein R is a heterocyclic aryl radical selected from the group consisting of radicals represented by the following structural formulas:

wherein A and A' are independently selected from the group consisting of hydrogen, lower alkyl, chlorine, and bromine, and G is selected from the group consisting of oxygen, nitrogen, and sulfur;

Y is leucyl, isoleucyl, nor-leucyl or N-methyl-leucyl;

Z is glycinamide or —NH—R¹, wherein

R¹ is lower alkyl, cycloalkyl, fluoro lower alkyl or

wherein

R² is hydrogen or lower alkyl;

or a pharmaceutical composition containing same.

20. A method of treating benign prostatic hypertrophy in a male mammalian subject which method comprises administering to said subject an effective amount of a compound of the formula (pyro)Glu—His—V—Ser—W—X—Y—Arg—Pro—Z  (I)

or a pharmaceutically acceptable salt thereof wherein:

V is tryptophyl, phenylalanyl or 3-(1-naphthyl)-L-alanyl;

W is tyrosyl, phenylalanyl or 3-(1-pentafluorophenyl)-L-alanyl;

X is a D-amino acid residue of the formula:

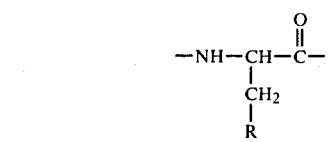

wherein R is a heterocyclic aryl radical selected from the group consisting of radicals represented by the following structural formulas:

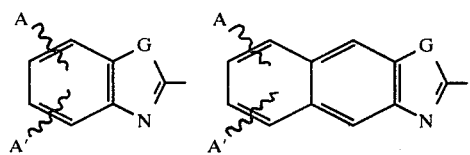
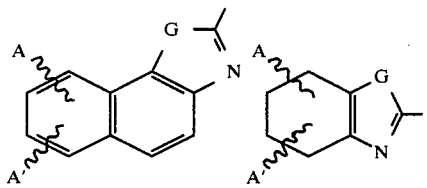
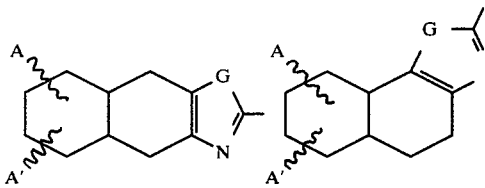

wherein A and A' are independently selected from the group consisting of hydrogen, lower alkyl, chlorine, and bromine, and G is selected from the group consisting of oxygen, nitrogen, and sulfur;
Y is leucyl, isoleucyl, nor-leucyl or N-methyl-leucyl;
Z is glycinamide or —NH—$R^1$, wherein
$R^1$ is lower alkyl, cycloalkyl, fluoro lower alkyl or

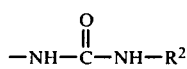

wherein
$R^2$ is hydrogen or lower alkyl;
or a pharmaceutical composition containing same.

21. A method of inhibiting spermatogenesis in a male mammalian subject which method comprises administering to said subject an effective amount of a compound of the formula:

(pyro)Glu—His—V—Ser—W—X—Y—Arg—Pro—Z     (I)

or a pharmaceutically acceptable salt thereof wherein:
V is tryptophyl, phenylalanyl or 3-(1-naphthyl)-L-alanyl;
W is tyrosyl, phenylalanyl or 3-(1-pentafluoro-phenyl)-L-alanyl;
X is a D-amino acid residue of the formula:

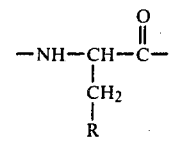

wherein R is a heterocyclic aryl radical selected from the group consisting of radicals represented by the following structural formulas:

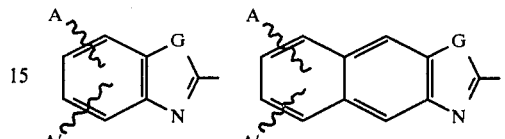
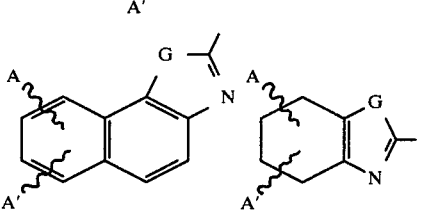
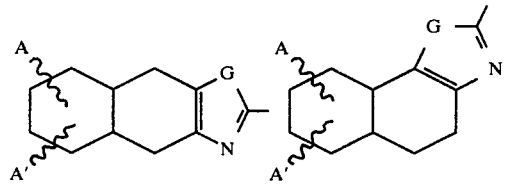

wherein A and A' are independently selected from the group consisting of hydrogen, lower alkyl, chlorine, and bromine, and G is selected from the group consisting of oxygen, nitrogen, and sulfur;
Y is leucyl, isoleucyl, nor-leucyl or N-methyl-leucyl;
Z is glycinamide or —NH—$R^1$, wherein
$R^1$ is lower alkyl, cycloalkyl, fluoro lower alkyl or

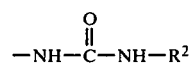

wherein
$R^2$ is hydrogen or lower alkyl;
or a pharmaceutical composition containing same.

22. A pharmaceutical composition for controlling effects of the LH/FSH releasing system of the anterior pituitary of a mammal, which comprises a therapeutically effective amount of a compound of claim 1 or a pharmaceutically acceptable acid addition salt thereof in admixture with a pharmaceutically acceptable excipient.

* * * * *